(12) United States Patent
Sato et al.

(10) Patent No.: US 9,908,941 B2
(45) Date of Patent: Mar. 6, 2018

(54) ANTI-HUMAN TSLP RECEPTOR ANTIBODY

(71) Applicant: Astellas Pharma Inc., Tokyo (JP)

(72) Inventors: Hiromu Sato, Tokyo (JP); Daisuke Yamajuku, Tokyo (JP); Kazunori Arai, Tokyo (JP); Mako Ogino, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 15/090,051

(22) Filed: Apr. 4, 2016

(65) Prior Publication Data

US 2016/0208005 A1    Jul. 21, 2016

Related U.S. Application Data

(60) Division of application No. 14/927,007, filed on Oct. 29, 2015, now Pat. No. 9,328,171, which is a continuation of application No. PCT/JP2014/071008, filed on Aug. 8, 2014.

(30) Foreign Application Priority Data

Aug. 9, 2013   (JP) ................................ 2013-165676

(51) Int. Cl.
| | |
|---|---|
| C07K 16/28 | (2006.01) |
| C07K 14/715 | (2006.01) |
| C12P 21/02 | (2006.01) |
| C07K 16/24 | (2006.01) |
| A61K 39/00 | (2006.01) |

(52) U.S. Cl.
CPC ........ *C07K 16/2866* (2013.01); *C07K 14/715* (2013.01); *C07K 16/244* (2013.01); *C12P 21/02* (2013.01); *A61K 2039/505* (2013.01); *C07K 2317/21* (2013.01); *C07K 2317/24* (2013.01); *C07K 2317/565* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS 7,731,953 B2   6/2010   Leonard et al.
8,344,110 B2   1/2013   Saris et al.

2012/0020960 A1   1/2012   Palucka et al.
2012/0020988 A1   1/2012   Auer et al.
2012/0027756 A1   2/2012   Dong et al.

FOREIGN PATENT DOCUMENTS

| JP | 2009-523426 A | 6/2009 |
|---|---|---|
| JP | 2010-530233 A | 9/2010 |
| JP | 2011-511638 A | 4/2011 |
| WO | 2007/112146 A2 | 10/2007 |
| WO | 2008/155365 A1 | 12/2008 |
| WO | 2009/100324 A1 | 8/2009 |
| WO | 2012/007495 A1 | 1/2012 |

OTHER PUBLICATIONS

International Search Report issued for PCT/JP2014/071008, mailed on Oct. 28, 2014, 8 pages.
Written Opinion issued Oct. 28, 2014 for PCT/JP2014/071008, 5 pages.
Donavan T. Cheng, et al., "Thymic stromal lymphopoietin receptor blockade reduces allergic inflammation in a cynomolgus monkey model of asthma", J Allergy Clin Immunol, Aug. 2013 pp. 455-462.
Office Action dated Jan. 23, 2017 issued in corresponding Singapore patent application No. 11201600935S.
Extended European Search Report dated Feb. 17, 2017 issued in corresponding European patent application No. 14833804.9.
Office Action dated Aug. 23, 2017 issued in corresponding European patent application No. 14 833 804.9.

*Primary Examiner* — Shulamith H Shafer
(74) *Attorney, Agent, or Firm* — Oblon, McClelland, Maier & Neustadt, L.L.P.

(57) ABSTRACT

An anti-human TSLP receptor antibody that specifically binds to human TSLP receptor and inhibits an action of human TSLP through human TSLP receptor. A method for preventing or treating asthma by administering the anti-human TSLP receptor antibody or an antigen-binding fragment thereof. An anti-human TSLP receptor antibody had been studied by the present inventors, and an anti-human TSLP receptor antibody including a heavy chain variable region consisting of the amino acid sequence of amino acid numbers 1 to 118 of SEQ ID NO: 1 and a light chain variable region consisting of the amino acid sequence of amino acid numbers 1 to 108 of SEQ ID NO: 3 was provided. It was revealed that the anti-human TSLP receptor antibody inhibits expression of TARC mRNA induced by TSLP and production of MDC proteins, and suppressed an allergic reaction in a monkey *Ascaris* antigen sensitization model.

13 Claims, 5 Drawing Sheets

SEQUENCE LISTING

```
<160> NUMBER OF SEQ ID NOS: 11

<210> SEQ ID NO 1
<211> LENGTH: 448
<212> TYPE: PRT
<213> ORGANISM: Artificial Sequence
<220> FEATURE:
<223> OTHER INFORMATION: H-chain of anti-human TSLP Receptor antibody

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Ser
            20                  25                  30

Ala Met His Trp Val Arg Gln Ala Pro Gly Lys Gly Leu Lys Trp Val
        35                  40                  45

Ser Ser Val Ser Gly Ser Gly Ala Gly Thr Tyr Tyr Ala Asp Ser Val
    50                  55                  60

Lys Gly Arg Phe Thr Ile Ser Arg Asp Asn Pro Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Glu Gly Gly Ser Arg Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

|  |  | 195 |  |  | 200 |  |  | 205 |  |  |  |
|---|---|---|---|---|---|---|---|---|---|---|---|

Asn Thr Lys Val Asp Lys Lys Val Glu Pro Lys Ser Cys Asp Lys Thr
    210                    215                    220

His Thr Cys Pro Pro Cys Pro Ala Pro Glu Leu Leu Gly Gly Pro Ser
225                    230                    235                    240

Val Phe Leu Phe Pro Pro Lys Pro Lys Asp Thr Leu Met Ile Ser Arg
                245                    250                    255

Thr Pro Glu Val Thr Cys Val Val Asp Val Ser His Glu Asp Pro
            260                    265                    270

Glu Val Lys Phe Asn Trp Tyr Val Asp Gly Val Glu Val His Asn Ala
              275                    280                    285

Lys Thr Lys Pro Arg Glu Glu Gln Tyr Asn Ser Thr Tyr Arg Val Val
    290                    295                    300

Ser Val Leu Thr Val Leu His Gln Asp Trp Leu Asn Gly Lys Glu Tyr
305                    310                    315                    320

Lys Cys Lys Val Ser Asn Lys Ala Leu Pro Ala Pro Ile Glu Lys Thr
                325                    330                    335

Ile Ser Lys Ala Lys Gly Gln Pro Arg Glu Pro Gln Val Tyr Thr Leu
          340                    345                    350

Pro Pro Ser Arg Asp Glu Leu Thr Lys Asn Gln Val Ser Leu Thr Cys
        355                    360                    365

Leu Val Lys Gly Phe Tyr Pro Ser Asp Ile Ala Val Glu Trp Glu Ser
370                    375                    380

Asn Gly Gln Pro Glu Asn Asn Tyr Lys Thr Thr Pro Pro Val Leu Asp
385                    390                    395                    400

Ser Asp Gly Ser Phe Phe Leu Tyr Ser Lys Leu Thr Val Asp Lys Ser
                405                    410                    415

Arg Trp Gln Gln Gly Asn Val Phe Ser Cys Ser Val Met His Glu Ala
          420                    425                    430

Leu His Asn His Tyr Thr Gln Lys Ser Leu Ser Leu Ser Pro Gly Lys
        435                    440                    445

```
<210> SEQ ID NO 2
<211> LENGTH: 1347
<212> TYPE: DNA
<213> ORGANISM: Artificial Sequence
<220> FEATURE:
<223> OTHER INFORMATION: H-chain gene of anti-human TSLP Receptor
      antibody

<400> SEQUENCE: 2
```

| | | | | |
|---|---|---|---|---|
| gaggtgcagc tgttggagtc tgggggaggc ttggtacagc cggggggttc cctgagactc | 60 |
| tcctgtgcag cctctggatt caccttcgc agctctgcca tgcattgggt ccgccaggct | 120 |
| ccagggaagg gactgaaatg ggtctcaagt gttagtggca gtggtgctgg aacatactac | 180 |
| gcagactccg tgaagggccg gttcaccatc tccagagaca atcccaagaa tacactgtat | 240 |
| ctgcaaatga acagtctgag agccgaggac acggccgtat attattgtgt gaaagaaggg | 300 |
| ggcagccggg gttttgacta ctggggccag ggaaccctgg tcaccgtctc ctcagcctcc | 360 |
| accaagggcc catcggtctt ccccctggca ccctcctcca agagcacctc tgggggcaca | 420 |
| gcggccctgg gctgcctggt caaggactac ttccccgaac cggtgacggt gtcgtggaac | 480 |
| tcaggcgccc tgaccagcgg cgtgcacacc ttcccggctg tcctacagtc ctcaggactc | 540 |
| tactccctta gtagcgtggt gaccgtgccc tccagcagct tgggcaccca gacctacatc | 600 |
| tgcaacgtga atcacaagcc cagcaacacc aaggtggaca agaaagttga gcccaaatct | 660 |

```
tgtgacaaaa ctcacacatg cccaccgtgc ccagcacctg aactcctggg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctccca gccccatcg agaaaaccat ctccaaagcc     1020
aaagggcagc ccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaatga                                        1347
```

<210> SEQ ID NO 3
<211> LENGTH: 214
<212> TYPE: PRT
<213> ORGANISM: Artificial Sequence
<220> FEATURE:
<223> OTHER INFORMATION: L-chain of anti-human TSLP Receptor antibody

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Thr Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Leu Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 4

<211> LENGTH: 645
<212> TYPE: DNA
<213> ORGANISM: Artificial Sequence
<220> FEATURE:
<223> OTHER INFORMATION: L-chain gene of anti-human TSLP Receptor antibody

<400> SEQUENCE: 4

```
gacatccaga tgacccagtc tccatcctca ctgtctgcat ctgtaggaga cagagtcacc     60
atcacttgtc gggcgagtca ggacattagc aattatttag cctggtttca gcagaaacca    120
gggaaagccc ctaagtccct gatctatact gcatccagtt tgcaaagtgg ggtcccatca    180
aagttcagcg gcagtggatc tgggacagat ttcactctca ccatcagcag cctgcagcct    240
gaagattttg caacttatta ctgccaacag tataatcttt atcctccgac gttcggccaa    300
gggaccaagg tggaaatcaa acggactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacctgacg    540
ctgagcaaag cagactacga aaacacaaa gtctacgcct gcgaagtcac ccatcagggc    600
ctgagctcgc ccgtcacaaa gagcttcaac aggggagagt gttag                    645
```

<210> SEQ ID NO 5
<211> LENGTH: 1395
<212> TYPE: DNA
<213> ORGANISM: Artificial Sequence
<220> FEATURE:
<223> OTHER INFORMATION: gene of human TSLP Receptor-human Fc

<400> SEQUENCE: 5

```
atgtctgtgc ctacccaggt gctgggactg ctgctgctgt ggctgacaga cgcccgctgt     60
ggagcagcag aaggagtaca gattcagatc atctacttca atttagaaac cgtgcaggtg    120
acatggaatg ccagcaaata ctccaggacc aacctgactt tccactacag attcaacggt    180
gatgaggcct atgaccagtg caccaactac cttctccagg aagtcacac ttcggggtgc    240
ctcctagacg cagagcagcg agacgacatt ctctatttct ccatcaggaa tgggacgcac    300
cccgttttca ccgcaagtcg ctggatggtt tattacctga acccagttc cccgaagcac    360
gtgagatttt cgtggcatca ggatgcagtg acggtgacgt tttctgacct gtcctacggg    420
gatctcctct atgaggttca gtaccggagc cccttcgaca ccgagtggca gtccaaacag    480
gaaaatacct gcaacgtcac catagaaggc ttggatgccg agaagtgtta ctcttttctgg    540
gtcagggtga aggctatgga ggatgtatat gggccagaca catacccaag cgactggtca    600
gaggtgacat gctggcagag aggcgagatt cgggatgcct gtgcagagac accaacgcct    660
cccaaaccaa agctgtccaa atcgaaggc aggatggacc ccaaatcttg tgacaaaact    720
cacacatgcc caccgtgccc agcacctgaa ctcctggggg gaccgtcagt cttcctcttc    780
cccccaaaac ccaaggacac cctcatgatc tcccggaccc ctgaggtcac atgcgtggtg    840
gtggacgtga gccacgaaga ccctgaggtc aagttcaact ggtacgtgga cggcgtggag    900
gtgcataatg ccaagacaaa gccgcgggag gagcagtaca acagcacgta ccgtgtggtc    960
agcgtcctca ccgtcctgca ccaggactgg ctgaatggca aggagtacaa gtgcaaggtc   1020
tccaacaaag ccctcccagc ccccatcgag aaaaccatct ccaaagccaa agggcagccc   1080
cgagaaccac aggtgtacac cctgccccca tcccgggatg agctgaccaa gaaccaggtc   1140
```

| | |
|---|---|
| agcctgacct gcctggtcaa aggcttctat cccagcgaca tcgccgtgga gtgggagagc | 1200 |
| aatgggcagc cggagaacaa ctacaagacc acgcctcccg tgctggactc cgacggctcc | 1260 |
| ttcttcctct acagcaagct caccgtggac aagagcaggt ggcagcaggg gaacgtcttc | 1320 |
| tcatgctccg tgatgcatga ggctctgcac aaccactaca cgcagaagag cctctccctg | 1380 |
| tctccgggta aatga | 1395 |

<210> SEQ ID NO 6
<211> LENGTH: 1437
<212> TYPE: DNA
<213> ORGANISM: Artificial Sequence
<220> FEATURE:
<223> OTHER INFORMATION: gene of human TSLP Receptor-mouse Fc

<400> SEQUENCE: 6

| | |
|---|---|
| atgtctgtgc ctacccaggt gctgggactg ctgctgctgt ggctgacaga cgcccgctgt | 60 |
| caggcagtgc acgccgcaca tgcagaaatc aacgaaggag cagcagaagg agtacagatt | 120 |
| cagatcatct acttcaattt agaaaccgtg caggtgacat ggaatgccag caaatactcc | 180 |
| aggaccaacc tgactttcca ctacagattc aacggtgatg aggcctatga ccagtgcacc | 240 |
| aactaccttc tccaggaagg tcacacttcg gggtgcctcc tagacgcaga gcagcgagac | 300 |
| gacattctct atttctccat caggaatggg acgcaccccg ttttcaccgc aagtcgctgg | 360 |
| atggtttatt acctgaaacc cagttccccg aagcacgtga attttcgtg catcaggat | 420 |
| gcagtgacgg tgacgtgttc tgacctgtcc tacgggatcc cctctatga ggttcagtac | 480 |
| cggagcccct tcgacaccga gtggcagtcc aaacaggaaa atacctgcaa cgtcaccata | 540 |
| gaaggcttgg atgccgagaa gtgttactct ttctgggtca gggtgaaggc tatggaggat | 600 |
| gtatatgggc cagacacata cccaagcgac tggtcagagg tgacatgctg gcagagaggc | 660 |
| gagattcggg atgcctgtgc agagacacca acgcctccca aaccaaagct gtccaaaatc | 720 |
| gaaggcagga tggacgagcc tcgaggtcct acaatcaagc cgtgtccacc ttgtaagtgc | 780 |
| cccgcgccaa atctgctggg tggtccttct gtattcatat ttccgcccaa gataaaagat | 840 |
| gtcttgatga tctctttgtc tccgatcgta acgtgcgtgg tcgtggatgt gtccgaagat | 900 |
| gaccctgacg ttcagatttc atggtttgtc aacaacgtgg aagtgcatac ggctcagact | 960 |
| cagacccacc gagaggatta caattccact ctgagagttg tgagcgctct tccgatccag | 1020 |
| caccaagatt ggatgagcgg gaaagaattt aagtgcaaag tgaacaataa ggaccttccc | 1080 |
| gcgcctatcg aaagaaccat atctaagcca aagggatccg tgcgagctcc acaggtgtac | 1140 |
| gtgctgcctc cgccagagga ggaaatgact aagaaacagg tgaccctcac atgcatggta | 1200 |
| accgacttca tgcctgaaga tatttacgtg gaatggacca caacggaaa accgaactc | 1260 |
| aactacaaaa acacagagcc cgttctggac tccgacggga gctacttcat gtactccaaa | 1320 |
| ctgagggtgg agaaaaagaa ttgggtggaa cgaaatagtt attcatgcag tgtagtccat | 1380 |
| gaggggctgc ataatcacca taccacaaag tctttcagca gaaccccctg gaaatga | 1437 |

<210> SEQ ID NO 7
<211> LENGTH: 1395
<212> TYPE: DNA
<213> ORGANISM: Artificial Sequence
<220> FEATURE:
<223> OTHER INFORMATION: gene of cynomolgus TSLP Receptor-human Fc

<400> SEQUENCE: 7

| | |
|---|---|
| atgtctgtgc ctacccaggt gctgggactg ctgctgctgt ggctgacaga cgcccgctgt | 60 |

```
gcaacaggag aaggactaca gattcagatc atctacttta atctagaaac ggtgcaggtg        120
acatggaatg ccagccacta ccccaggagt aacctgagtt tccactacaa attcagtcga        180
gatgaggcct atgaccagtg caccgtctac attctccagg aaggtcacac ctcggggtgc        240
ctcctagacg cagagcagca agacgatatt ctgtatttct ccatcaggaa cgggacgcac        300
cccgttttca ccgccagtcg ctggatcttt tattacctga agcccagttc tccgaagcag        360
gtgagctttt cgtggcatca ggacgcggtg acagtgacgt gctctgacct gtcctacagg        420
ggtctcctct atgaggttca gtaccggagc cccttcgaca cggagtggca gtccaaacag        480
gaaaatacct gcaatgtcac tatagaagac ttggatgccg agaagtgtta tgctttccgg        540
gcccgggtga aggccatgga ggatgcgtat gggccggaca cgtacccgag cgactggtca        600
gaggtgacgt gctggcagag aggcgagact cgcgattcgt gcccagagcc tcgcacgcct        660
cccaaaccga agctgtccaa aatcgaaggc aggatggacc ccaaatcttg tgacaaaact        720
cacacatgcc caccgtgccc agcacctgaa ctcctggggg gaccgtcagt cttcctcttc        780
cccccaaaac ccaaggacac cctcatgatc tcccggaccc ctgaggtcac atgcgtggtg        840
gtggacgtga gccacgaaga ccctgaggtc aagttcaact ggtacgtgga cggcgtggag        900
gtgcataatg ccaagacaaa gccgcgggag gagcagtaca acagcacgta ccgtgtggtc        960
agcgtcctca ccgtcctgca ccaggactgg ctgaatggca aggagtacaa gtgcaaggtc       1020
tccaacaaag ccctcccagc ccccatcgag aaaaccatct ccaaagccaa agggcagccc       1080
cgagaaccac aggtgtacac cctgccccca tcccgggatg agctgaccaa gaaccaggtc       1140
agcctgacct gcctggtcaa aggcttctat cccagcgaca tcgccgtgga gtgggagagc       1200
aatgggcagc cggagaacaa ctacaagacc acgcctcccg tgctggactc cgacggctcc       1260
ttcttcctct acagcaagct caccgtggac aagagcaggt ggcagcaggg gaacgtcttc       1320
tcatgctccg tgatgcatga ggctctgcac aaccactaca cgcagaagag cctctccctg       1380
tctccgggta aatga                                                        1395

<210> SEQ ID NO 8
<211> LENGTH: 483
<212> TYPE: DNA
<213> ORGANISM: Artificial Sequence
<220> FEATURE:
<223> OTHER INFORMATION: gene of human TSLP mutant-Flag

<400> SEQUENCE: 8
atgtctgtgc ctacccaggt gctgggactg ctgctgctgt ggctgacaga cgcccgctgt         60
tacgacttca ctaactgtga ctttgagaag attaaagcag cctatctcag tactatttct        120
aaagacctga ttacatatat gagtgggacc aaaagtactg agttcaacaa caccgtctct        180
tgtagcaatc ggccacattg ccttactgaa atccagagcc taaccttcaa tcccaccgcc        240
ggctgcgcgt cgctcgccaa agaaatgttc gccatgaaaa ctaaggctgc cttagctatc        300
tggtgcccag gctattcgga aactcagata aatgctactc aggcaatgaa gaagaggaga        360
aaagccaaag tcacaaccaa taatgtctg gaacaagtgt cacaattaca aggattgtgg        420
cgtcgcttca atcgaccttt actgaaacaa caggactaca aggacgacga tgacaaatga        480
taa                                                                      483

<210> SEQ ID NO 9
<211> LENGTH: 498
<212> TYPE: DNA
```

<213> ORGANISM: Artificial Sequence
<220> FEATURE:
<223> OTHER INFORMATION: gene of cynomolgus TSLP mutant-Flag

<400> SEQUENCE: 9

```
atggagacag acacactcct gctatgggta ctgctgctct gggttccagg ttccaccggt      60
tacgacttca ctaactgtga cttttcagaag attgaagcag actatctccg tactatttct    120
aaagacctga ttacatatat gagtgggact aaaagtaccg acttcaacaa caccgtctcc     180
tgtagcaatc ggccacactg ccttactgaa atccagagcc taaccttcaa tcccaccccc     240
cgctgcgcgt cgctcgccaa ggaaatgttc gccaggaaaa ctaaggctac cctcgctctc     300
tggtgcccag ctattcgga aactcagata atgctactc aggcaatgaa gaagaggaga       360
aaagccaaag tcacaaccaa taatgtctg gaacaagtgt cacaattact aggattgtgg      420
cgtcgcttca ttcgaacttt actgaaacaa cagcaccacc accaccacca tgactataaa    480
gacgatgacg acaaatga                                                    498
```

<210> SEQ ID NO 10
<211> LENGTH: 1116
<212> TYPE: DNA
<213> ORGANISM: Homo sapiens

<400> SEQUENCE: 10

```
atggggcggc tggttctgct gtggggagct gccgtctttc tgctgggagg ctggatggct      60
ttggggcaag gaggagcagc agaaggagta cagattcaga tcatctactt caatttagaa     120
accgtgcagg tgacatggaa tgccagcaaa tactccagga ccaacctgac tttccactac     180
agattcaacg gtgatgaggc ctatgaccag tgcaccaact accttctcca ggaaggtcac     240
acttcggggt gcctcctaga cgcagagcag cgagacgaca ttctctattt ctccatcagg     300
aatgggacgc accccgtttt caccgcaagt cgctggatgg tttattacct gaaacccagt     360
tccccgaagc acgtgagatt ttcgtggcat caggatgcag tgacggtgac gtgttctgac     420
ctgtcctacg gggatctcct ctatgaggtt cagtaccgga gccccttcga caccgagtgg     480
cagtccaaac aggaaaatac ctgcaacgtc accatagaag gcttggatgc cgagaagtgt    540
tactctttct gggtcagggt gaaggctatg gaggatgtat atgggccaga cacatacca    600
agcgactggt cagaggtgac atgctggcag agaggcgaga ttcggatgc ctgtgcagag    660
acaccaacgc ctcccaaacc aaagctgtcc aaatttattt taatttccag cctggccatc   720
cttctgatgg tgtctctcct ccttctgtct ttatggaaat tatggagagt gaggaagttt   780
ctcattccca gcgtgccaga cccgaaatcc atcttccccg ggctctttga gatacaccaa   840
gggaacttcc aggagtggat cacagacacc agaacgtgg cccacctcca caagatggca    900
ggtgcagagc aagaaagtgg ccccgaggag cccctggtag tccagttggc caagactgaa   960
gccgagtctc ccaggatgct ggacccacag accgaggaga agaggcctc tggggatcc    1020
ctccagcttc cccaccagcc cctccaaggt ggtgatgtgg tcacaatcgg gggcttcacc   1080
tttgtgatga atgaccgctc ctacgtggcg ttgtga                             1116
```

<210> SEQ ID NO 11
<211> LENGTH: 1380
<212> TYPE: DNA
<213> ORGANISM: Homo sapiens

<400> SEQUENCE: 11

```
atgacaattc taggtacaac ttttggcatg gttttttctt tacttcaagt cgtttctgga     60
```

```
gaaagtggct atgctcaaaa tggagacttg gaagatgcag aactggatga ctactcattc      120
tcatgctata gccagttgga agtgaatgga tcgcagcact cactgacctg tgcttttgag      180
gacccagatg tcaacatcac caatctggaa tttgaaatat gtggggccct cgtggaggta      240
aagtgcctga atttcaggaa actacaagag atatatttca tcgagacaaa gaaattctta      300
ctgattggaa agagcaatat atgtgtgaag gttggagaaa agagtctaac ctgcaaaaaa      360
atagacctaa ccactatagt taaacctgag gctcctttg acctgagtgt cgtctatcgg       420
gaaggagcca atgactttgt ggtgacattt aatacatcac acttgcaaaa gaagtatgta      480
aaagttttaa tgcacgatgt agcttaccgc caggaaaagg atgaaaacaa atggacgcat      540
gtgaatttat ccagcacaaa gctgacactc ctgcagagaa agctccaacc ggcagcaatg      600
tatgagatta aagttcgatc catccctgat cactatttta aaggcttctg gagtgaatgg      660
agtccaagtt attacttcag aactccagag atcaataata gctcagggga gatggatcct      720
atcttactaa ccatcagcat tttgagtttt ttctctgtcg ctctgttggt catcttggcc      780
tgtgtgttat ggaaaaaaag gattaagcct atcgtatggc ccagtctccc cgatcataag      840
aagactctgg aacatctttg taagaaacca agaaaaaatt taaatgtgag tttcaatcct      900
gaaagtttcc tggactgcca gattcatagg gtggatgaca ttcaagctag agatgaagtg      960
gaaggttttc tgcaagatac gtttcctcag caactagaag aatctgagaa gcagaggctt     1020
ggaggggatg tgcagagccc caactgccca tctgaggatg tagtcatcac tccagaaagc     1080
tttggaagag attcatccct cacatgcctg gctgggaatg tcagtgcatg tgacgcccct     1140
attctctcct cttccaggtc cctagactgc agggagagtg gcaagaatgg gcctcatgtg     1200
taccaggacc tcctgcttag ccttgggact acaaacagca cgctgccccc tccattttct     1260
ctccaatctg gaatcctgac attgaaccca gttgctcagg gtcagcccat tcttacttcc     1320
ctgggatcaa atcaagaaga agcatatgtc accatgtcca gcttctacca aaaccagtga     1380
```

ANTI-HUMAN TSLP RECEPTOR ANTIBODY

CROSS REFERENCE TO RELATED APPLICATIONS

The present application is a Divisional of U.S. Ser. No. 14/927,007, filed on Oct. 29, 2015, which is a Continuation of International patent application PCT/JP2014/071008, filed on Aug. 8, 2014, and claims the benefit of the filing date of Japanese application no. 2013-165676, filed on Aug. 9, 2013, the text of each of which is incorporated by reference.

TECHNICAL FIELD

The present invention relates to a novel anti-human TSLP receptor antibody.

BACKGROUND ART

Thymic stromal lymphopoietin (TSLP) is a cytokine derived from epithelium cells, which is produced in response to pro-inflammatory stimuli. Mainly, TSLP enhances an allergic inflammatory response through the activation of dendritic cells and mast cells. The dendritic cells express TSLP receptor and IL-7 receptor α-chain which are members of a hematopoietic receptor family, and TSLP binds to a heterodimer consisting of TSLP receptor and IL-7 receptor α chain, thereby activating the dendritic cells. The dendritic cells activated by TSLP express inflammatory chemokines such as thymus and activation regulated chemokines (TARC (CCL17)), macrophage-derived chemokines (MDC (CCL22)), and the like (Nat. Immunol., 2002, Vol. 7, p. 673 to 680). It has been known that TARC and MDC are Th2 chemokines and attract Th2 cells to an inflammation site (Int. Immunol., 1999, Vol. 11, p. 81 to 88). Further, the dendritic cells activated by TSLP strongly induce the differentiation of naïve T cells into Th2 cells, and the Th2 cells produce IL-4, IL-5, IL-13, and TNFα, and cause the inflammatory reaction (Nat. Immunol., 2002, Vol. 7, p. 673 to 680).

It has been reported that the activation of the dendritic cells due to TSLP through such TSLP receptor is involved with disease pathology, including allergic inflammatory diseases such as asthma, and systemic sclerosis.

With regard to asthma, it has been reported that in transgenic mice in which the TSLP expression is enhanced specifically in a lung, the inflammatory response in an airway is caused accompanied by an increase of the amount of IgE and the Th2 cytokines in a lung, and this leads to asthmatic pathology (Nat. Immunol., 2005, Vol. 6, p. 1047 to 1053). Further, in knockout mice of TSLP receptor or an asthma model to which an anti-TSLP receptor antibody is administered, the suppression of Th2 cytokines and IgE production in the blood, and the improvement of respiratory function have been observed (J. Exp. Med., 2005, Vol. 202, p. 829 to 839, and Clin. Immunol., 2008, Vol. 129. p. 202 to 210). In addition, in asthma patients, it has been reported that expressions of TSLP, TARC, and MDC increases in the asthmatic airways in correlation with the severity of the disease (J. Immunol., 2005, Vol. 174, p. 8183 to 8190, and J. Immunol., 2008, Vol. 181, p. 2790 to 2798).

With respect to systemic sclerosis, it has been reported that TSLP is overexpressed in the skin of systemic sclerosis patients (Arthritis Rheum., 2013, Vol. 65, p. 1335 to 1346), and that expression of IL-13 and IL-17 in inflammation site of skin is almost completely suppressed and the proportion of collagen to histopathology was significantly improved in a bleomycin-induced scleroderma model using TSLP receptor-knockout mice (Ann. Rheum. Dis., 2013, Vol. 72, p. 2018 to 2023).

Accordingly, when a monoclonal antibody that specifically binds to human TSLP receptor and inhibits an action of human TSLP through human TSLP receptor can be developed, it is expected that such antibody is useful for preventing and treating various diseases in which human TSLP and human TSLP receptor are involved in disease pathology.

As antibodies against human TSLP receptor for which research has been conducted so far, 13H5 as a mouse monoclonal antibody and hu13H5 as a humanized antibody thereof (Patent Document 1), 1D6.C9 as a mouse monoclonal antibody and Nv115-3B-IgG1 and NV115-3B-IgG4 as chimeric antibodies thereof (Patent Document 2), NV164-1 and NV163-1 as fully human antibodies (Patent Document 3), and TSLPR-012_141 as a humanized monoclonal antibody derived from a hamster have been reported.

In 13H5, neutralizing activity has been confirmed in a TSLP-induced proliferation assay using Ba/F3 cells stably expressing human TSLP receptor, but neutralizing activity in hu13H5 has not been confirmed yet (Patent Document 1). Further, based on description of Patent Documents 2 to 4, among the antibodies described in these documents, it is recognized that TSLPR-012_141 has the highest neutralizing activity (Patent Documents 2 to 4). TSLPR-012_141 has been evaluated through various tests of neutralizing activity. For example, in the TSLP-induced proliferation assay using Ba/F3 cells stably expressing human TSLP receptor, TSLP-induced TARC, MDC, and IL-8 production assay using human peripheral blood-derived dendritic cells, TSLP-induced Th2 cytokine production assay using human peripheral blood-derived dendritic cells and naïve T cell co-culture systems, and the like, TSLPR-012_141 has been confirmed to show the neutralizing activity (Patent Document 4). However, an antibody showing high neutralizing activity for being used as antibody drug is desirable.

The main factors that determine the effective dosage of an antibody drug include binding activity and neutralizing activity of the antibody against an antigen as well as an amount of the antigen which is present in the body. An increase of the binding activity and neutralizing activity leads to reduction in dosage, and as a result, leads to reduction in financial burden and medical expenses of patients, which is an extremely beneficial improvement.

Therefore, it is necessary to obtain an anti-human TSLP receptor antibody which is excellent in activity compared to the conventional anti-human TSLP receptor antibody to be used for preventing and treating various diseases.

RELATED ART

Patent Document

[Patent Document 1] WO 2009/100324
[Patent Document 2] WO 2007/112146
[Patent Document 3] WO 2008/155365
[Patent Document 4] WO 2012/007495

DISCLOSURE OF INVENTION

Problems to be Solved by the Invention

An object of the present invention is to provide an anti-human TSLP receptor antibody that is specifically binds to human TSLP receptor and inhibits an action of human TSLP through human TSLP receptor.

Means for Solving the Problems

As a result of intensive research on production of the anti-human TSLP receptor antibody by the present inventors, an anti-human TSLP receptor antibody comprising a heavy chain variable region consisting of the amino acid sequence of amino acid numbers 1 to 118 of SEQ ID NO: 1 and a light chain variable region consisting of the amino acid sequence of amino acid numbers 1 to 108 of SEQ ID NO: 3 was provided. It was revealed that the anti-human TSLP receptor antibody inhibited TARC mRNA expression and MDC proteins production induced by TSLP (Examples 5 and 6), and suppressed an allergic reaction in a monkey *Ascaris* antigen sensitization model (Example 7), thereby completing the present invention.

That is, the present invention includes the following as a material or a method which is medically or industrially useful:

(1) An anti-human TSLP receptor antibody or an antigen-binding fragment thereof, comprising a heavy chain variable region consisting of the amino acid sequence of amino acid numbers 1 to 118 of SEQ ID NO: 1, and a light chain variable region consisting of the amino acid sequence of amino acid numbers 1 to 108 of SEQ ID NO: 3.

(2) The anti-human TSLP receptor antibody or the antigen-binding fragment thereof of (1) above, wherein a heavy chain constant region of the antibody is a human Igγ1 constant region.

(3) The anti-human TSLP receptor antibody or the antigen-binding fragment thereof of (1) above, wherein a light chain constant region of the antibody is a human Igκ constant region.

(4) The anti-human TSLP receptor antibody or the antigen-binding fragment thereof of (1) above, wherein a heavy chain constant region of the antibody is a human Igγ1 constant region, and a light chain constant region of the antibody is a human Igκ constant region.

(5) The antigen-binding fragment of any one of (1) to (4) above, wherein the antigen-binding fragment is a single-chain variable region fragment, Fab, Fab', or F(ab')$_2$.

(6) The anti-human TSLP receptor antibody of (1) above, comprising the heavy chain consisting of the amino acid sequence shown by SEQ ID NO: 1 and the light chain consisting of the amino acid sequence shown by SEQ ID NO: 3.

(7) The anti-human TSLP receptor antibody of (1) above, comprising the heavy chain consisting of the amino acid sequence of amino acid numbers 1 to 447 of SEQ ID NO: 1, and the light chain consisting of the amino acid sequence shown by SEQ ID NO. 3.

(8) A polynucleotide comprising a base sequence encoding the heavy chain variable region of the antibody of (1) above.

(9) A polynucleotide comprising a base sequence encoding the light chain variable region of the antibody of (1) above.

(10) An expression vector comprising the polynucleotide of (8) and/or (9) above.

(11) A host cell transformed with the expression vector of (10) above, which is selected from the group consisting of the following (a) to (d):

(a) a host cell transformed with an expression vector comprising a polynucleotide comprising a base sequence encoding the heavy chain variable region of the anti-human TSLP receptor antibody of (1) above and a polynucleotide comprising a base sequence encoding the light chain variable region of the antibody;

(b) a host cell transformed with an expression vector comprising a polynucleotide comprising the base sequence encoding the heavy chain variable region of the anti-human TSLP receptor antibody of (1) above and an expression vector comprising a polynucleotide comprising the base sequence encoding the light chain variable region of the antibody;

(c) a host cell transformed with an expression vector comprising a polynucleotide comprising the base sequence encoding the heavy chain variable region of the anti-human TSLP receptor antibody of (1) above; and (d) a host cell transformed with an expression vector comprising a polynucleotide comprising the base sequence encoding the light chain variable region of the anti-human TSLP receptor antibody of (1) above.

(12) A host cell transformed with the expression vector of (10) above, which is selected from the group consisting of the following (a) to (d):

(a) a host cell transformed with an expression vector comprising a polynucleotide comprising the base sequence encoding the heavy chain of the anti-human TSLP receptor antibody of (6) above and a polynucleotide comprising the base sequence encoding the light chain of the antibody;

(b) a host cell transformed with an expression vector comprising a polynucleotide comprising the base sequence encoding the heavy chain of the anti-human TSLP receptor antibody of (6) above and an expression vector comprising a polynucleotide comprising the base sequence encoding the light chain of the antibody;

(c) a host cell transformed with an expression vector comprising a polynucleotide comprising the base sequence encoding the heavy chain of the anti-human TSLP receptor antibody of (6) above; and (d) a host cell transformed with an expression vector comprising a polynucleotide comprising the base sequence encoding the light chain of the anti-human TSLP receptor antibody of (6) above.

(13) A method of producing the anti-human TSLP receptor antibody or an antigen-binding fragment thereof, which comprises culturing the host cell of (11) above to express an anti-human TSLP receptor antibody or an antigen-binding fragment thereof.

(14) A method of producing the anti-human TSLP receptor antibody, which comprises culturing the host cell of (12) above to express an anti-human TSLP receptor antibody.

(15) An anti-human TSLP receptor antibody or an antigen-binding fragment thereof produced by the method of (13) above.

(16) An anti-human TSLP receptor antibody produced by the method of (14) above.

(17) A pharmaceutical composition comprising the anti-human TSLP receptor antibody or the antigen-binding fragment thereof of any one of (1) to (7), (15) and (16) above and a pharmaceutically acceptable excipient.

(18) The pharmaceutical composition of (17) above, which is the pharmaceutical composition for preventing or treating asthma.

(19) A method for preventing or treating asthma, which comprises administrating a therapeutically effective amount of the anti-human TSLP receptor antibody or the antigen-binding fragment thereof of any one of (1) to (7), (15) and (16) above.

(20) The anti-human TSLP receptor antibody or the antigen-binding fragment thereof of any one of (1) to (7), (15) and (16) above, for use in preventing or treating asthma.

(21) Use of the anti-human TSLP receptor antibody or the antigen-binding fragment thereof of any one of (1) to (7), (15) and (16) above for manufacture of a pharmaceutical composition for preventing or treating asthma.

The anti-human TSLP receptor antibody or the antigen-binding fragment thereof of (1) to (7), (15) and (16) above includes a fusion of the antibody or the antigen-binding fragment thereof and another peptide or protein, and a modification having a modifying agent bound thereto.

Effects of the Invention

The anti-human TSLP receptor antibody of the present invention binds to human TSLP receptor, has neutralizing activity against an action of human TSLP through human TSLP receptor, and can be used as an agent for preventing or treating allergic inflammatory diseases such as asthma or systemic sclerosis.

EMBODIMENTS FOR CARRYING OUT THE INVENTION

Figure 1:
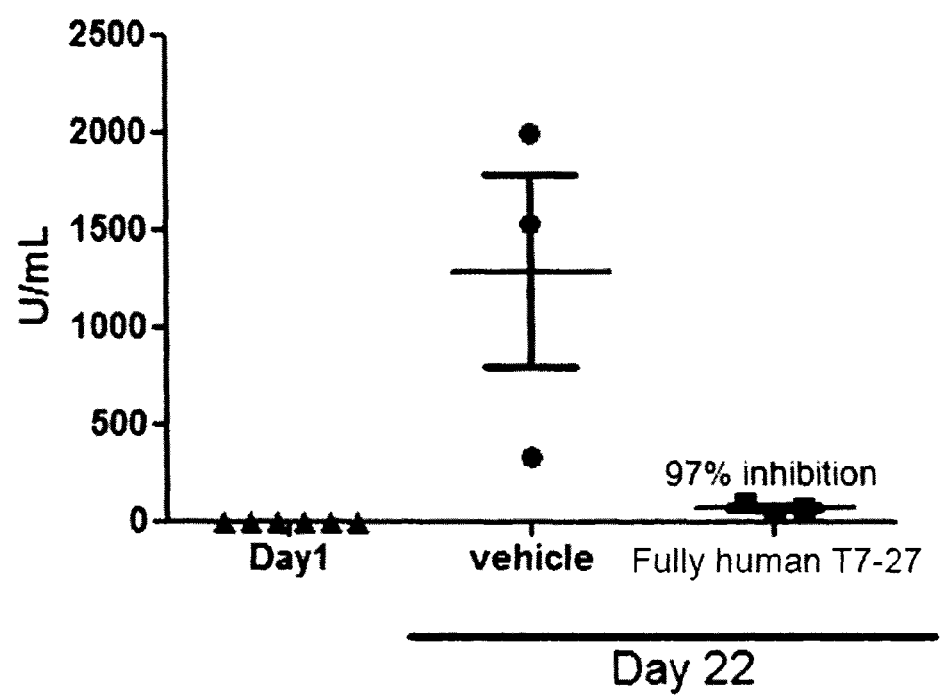
FIG. 1 shows an inhibitory action of fully human T7-27 on *Ascaris* antigen-specific IgE concentration in a monkey *Ascaris* antigen sensitization model. The vertical axis represents relative plasma *Ascaris* antigen-specific IgE concentration of respective samples when the plasma *Ascaris* antigen-specific IgE concentration in Day 22 of one individual from among a Vehicle group is set to 2000 U/mL. IgE concentration on Day 1 of the Vehicle group and an antibody administration group (before administering an *Ascaris* antigen liquid suspended by aluminum hydroxide gel), IgE concentration on Day 22 of the Vehicle group, and IgE concentration on Day 22 of the antibody administration group are shown.

Hereinafter, the present invention will be described in detail.

There are five classes of IgG, IgM, IgA, IgD, and IgE in an antibody, and the basic structure of an antibody molecule is configured of heavy chains having a molecular weight of 50000 to 70000 and light chains having a molecular weight of 20000 to 30000 in each of the classes in common. Heavy chain usually consists of a polypeptide chain comprising approximately 440 amino acids, has a distinctive structure for each of the classes, and is referred to as Igγ, Igμ, Igα, and Igε corresponding to IgG, IgM, IgA, IgD, and IgE, respectively. Further, four subclasses of IgG1, IgG2, IgG3, and IgG4 are present in IgG, and the heavy chains respectively corresponding thereto are referred to as Igγ1, Igγ2, Igγ3, and Igγ4. Light chain usually consists of a polypeptide chain comprising 220 amino acids, two types of which, type L and type K are known, and are referred to as Igλ and Igκ. In a peptide configuration of the basic structure of antibody molecules, two homologous heavy chains and two homologous light chains are bound by disulfide bonds (S—S bond) and non-covalent bonds, and the molecular weight thereof is 150000 to 190000. Two kinds of light chains can be paired with any heavy chain. The respective antibody molecules typically consist of two identical light chains and two identical heavy chains.

With regard to intrachain S—S bonds, four of the S—S bonds are present in the heavy chain (five in Igμ and Igε) and two of them are present in the light chain; one loop is formed per 100 to 110 amino acid residues, and this steric structure is similar among the loops and are referred to as a structural unit or a domain. The domain located at the amino terminal (N terminal) side in both of the heavy chain and the light chain, whose amino acid sequence is not constant even in a case of a sample from the same class (sub class) of the same kind of animal is referred to as a variable region, and respective domains are referred to as a heavy chain variable region ($V_H$) and a light chain variable region ($V_L$). The amino acid sequence of a carboxy terminal (C terminal) side from the variable region is nearly constant in each class or subclass and is referred to as a constant region (each of the domains is called $C_H1$, $C_H2$, $C_H3$ and $C_L$, respectively).

An antigenic determinant site of an antibody is configured of $V_H$ and $V_L$, and the binding specificity depends on the amino acid sequence of this site. On the other hand, biological activities such as binding to complements and various cells reflect differences in the constant region structures among each class Ig. It is understood that the variability of variable regions of the light chains and the heavy chains is mostly limited to three small hypervariable regions present in both chains and these regions are referred to as complementarity determining regions (CDR: CDR1, CDR2, and CDR3 from the N terminal side). The remaining portion of the variable region is referred to as a framework region (FR) and is relatively constant.

Further, various kinds of antigen-binding fragments comprising $V_H$ and $V_L$ of an antibody have antigen binding activity. For example, a single-chain variable region fragment (scFv), Fab, Fab', and F(ab')$_2$ are exemplified as typical antigen-binding fragments. A Fab is a monovalent antigen-binding fragment which is constituted with a light-chain and a heavy-chain fragment including a $V_H$, a $C_H1$, and a portion of the hinge region. A Fab' is a monovalent antigen-binding fragment which is constituted with a light-chain and a heavy-chain fragment including a $V_H$, a $C_H1$, and a portion of the hinge region, and cysteine residues constituting the inter-heavy-chain S—S bond are included in the portion of the hinge region. A F(ab')$_2$ is a bivalent antigen-binding fragment having a dimeric structure in which two Fab' fragments bind to each other via the inter-heavy-chain S—S bond in the hinge region. An scFv is a monovalent antigen-binding fragment which is constituted with a $V_H$ and $V_L$ connected with a linker peptide.

Anti-Human TSLP Receptor Antibody of the Present Invention

An anti-human TSLP receptor antibody or antigen-binding fragment thereof of the present invention is an anti-human TSLP receptor antibody or antigen-binding fragment thereof having the following characteristics.

An anti-human TSLP receptor antibody or an antigen-binding fragment thereof comprises the heavy chain variable region consisting of the amino acid sequence of amino acid numbers 1 to 118 of SEQ ID NO: 1, and a light chain variable region consisting of the amino acid sequence of amino acid numbers 1 to 108 of SEQ ID NO: 3.

Preferably, the anti-human TSLP receptor antibody or the antigen-binding fragment thereof of the present invention has the above-described characteristics and further comprises a heavy chain constant region and a light chain constant region. As the constant region, any subclasses of constant region (for example, a constant region of Igγ1, Igγ2, Igγ3, or Igγ4 as the heavy chain constant region and a constant region of Igλ or Igκ as the light chain constant region) can be selected, but human Igγ1 constant region is preferable as the heavy chain constant region and human Igκ constant region is preferable as a light chain constant region.

A human Igγ1 constant region includes, for example, human Igγ1 constant region consisting of the amino acid sequence of amino acid numbers 119 to 448 of SEQ ID NO:1.

A human Igκ constant region includes, for example, human Igκ constant region consisting of the amino acid sequence of amino acid numbers 109 to 214 of SEQ ID NO:3.

As the anti-human TSLP receptor antibody or the antigen-binding fragment thereof of the present invention, the anti-human TSLP receptor antibody or the antigen-binding fragment thereof comprising the above-described heavy chain variable region and the light chain variable region and in which the heavy chain constant region is the human Igγ1 constant region and the light chain constant region is the human Igκ constant region is further preferable.

In one embodiment, the antigen-binding fragment of the present invention is scFv, Fab, Fab', or F(ab')$_2$.

Any person skilled in the art can construct a fusion of an antibody or an antigen-binding fragment thereof and another peptide or protein and can also construct a modification having a modifying agent bound thereto, using a known method in the field. The antibody or the antigen-binding fragment thereof of the present invention includes the antibody and the antigen-binding fragment thereof in the form of such a fusion or a modification. For example, an anti-human TSLP receptor antibody or an antigen-binding fragment thereof comprising the heavy chain variable region consisting of the amino acid sequence of amino acid numbers 1 to 118 of SEQ ID NO: 1, and a light chain variable region consisting of the amino acid sequence of amino acid numbers 1 to 108 of SEQ ID NO: 3 includes a fusion of the antibody or the antigen-binding fragment thereof and another peptide or protein, and a modification having a modifying agent bound thereto. The other peptide or protein used for the fusion is not particularly limited, so long as it does not reduce the binding activity of the antibody or the antigen-binding fragment thereof; examples thereof include human serum albumin, various tag peptides, artificial helix motif peptide, maltose-binding proteins, glutathione S transferase, various toxins, other peptides or proteins capable of promoting multimerization, and the like. The modifying agent used for the modification is not particularly limited, so long as it does not reduce the binding activity of the antibody or the antigen-binding fragment thereof; examples thereof include polyethylene glycol, sugar chains, phospholipids, liposomes, low-molecular compounds and the like.

In one embodiment, the anti-human TSLP receptor antibody of the present invention is an anti-human TSLP receptor antibody having the following characteristics.

An anti-human TSLP receptor antibody comprising the heavy chain consisting of the amino acid sequence shown by SEQ ID NO: 1 and the light chain consisting of the amino acid sequence shown by SEQ ID NO: 3.

In a case where an antibody is expressed in cells, it is known that the antibody is modified after translation. Examples of post-translational modification include cutting of lysine of a C terminal of a heavy chain by carboxypeptidase, modification to pyroglutamic acid due to pyroglutamylation of glutamic acid or glutamine of an N terminal of a heavy chain or a light chain, and the like. It is known that lysine of the C terminal of the heavy chain is deleted or a large part of glutamine of the N terminal of the heavy chain is modified to pyroglutamic acid (Journal of Pharmaceutical Sciences, 2008, Vol. 97, p. 2426). Further, it is also known that the modification after translation does not influence the activity of an antibody in the field (Analytical Biochemistry, 2006, Vol. 348, p. 24 to 39).

The antibody of the present invention includes an antibody modified after translation during expression in cells such as an antibody comprising a heavy chain lacking lysine of a C terminal, an antibody in which glutamine or glutamic acid of the N terminal of the heavy chain is modified to pyroglutamic acid due to pyroglutamylation, and the like in addition to an antibody comprising a full length of heavy chain. Further, the antigen-binding fragment of the present invention includes an antigen-binding fragment modified after translation during expression in cells such as an antigen-binding fragment in which glutamine or glutamic acid of the N terminal of the heavy chain is modified to pyroglutamic acid due to pyroglutamylation.

For example, the anti-human TSLP receptor antibody of the invention includes an anti-human TSLP receptor antibody described below.

An anti-human TSLP receptor antibody comprising the heavy chain consisting of the amino acid sequence shown by SEQ ID NO: 1, in which glutamic acid of the amino acid number 1 of SEQ ID NO: 1 is modified to pyroglutamic acid and/or lysine of the amino acid number 448 of SEQ ID NO: 1 is deleted, and the light chain consisting of the amino acid sequence shown by SEQ ID NO: 3.

The present invention includes an anti-human TSLP receptor antibody or an antigen-binding fragment thereof having the following characteristics.

An anti-human TSLP receptor antibody or an antigen-binding fragment thereof comprising a heavy chain variable region comprising CDR1 consisting of the amino acid sequence of amino acid numbers 31 to 35 of SEQ ID NO: 1, CDR2 consisting of the amino acid sequence of amino acid numbers 50 to 66 of SEQ ID NO: 1, and CDR3 consisting of the amino acid sequence of amino acid numbers 99 to 107 of SEQ ID NO:1, and the light chain variable region comprising CDR1 consisting of the amino acid sequence of amino acid numbers 24 to 34 of SEQ ID NO: 3, CDR2 consisting of the amino acid sequence of amino acid numbers 50 to 56 of SEQ ID NO: 3, and CDR3 consisting of the amino acid sequence of amino acid numbers 89 to 97 of SEQ ID NO:3.

The anti-human TSLP receptor antibody or the antigen-binding fragment thereof of the present invention binds to human TSLP receptor. Whether the antibody or the antigen-binding fragment thereof binds to human TSLP receptor is confirmed by using a binding activity measurement method in the related art. Examples of the method of measuring the binding activity include a method of Enzyme-linked immunosorbent assay (ELISA) or a method of surface plasmon resonance (SPR). In a case of using the ELISA, in an exemplary method, a fusion protein of human TSLP receptor and human Fc (human TSLP receptor-human Fc fusion protein (being encoded by the base sequence of SEQ ID NO: 5)) is immobilized on an ELISA plate, and a test antibody is added thereto to be reacted. After the reaction, a secondary antibody such as an anti-IgG antibody or the like labeled with an enzyme such as Horseradish peroxidase (HRP) is reacted, and washed, and then it is possible to confirm whether the test antibody binds to human TSLP receptor with activity measurement using a reagent detecting the activity (for example, in a case of HRP labeling, BM-Chemiluminescence ELISA Substrate (POD) (Roche Diagnostics. Inc.)). In the case of using SPR, for example, it is possible to use Biacore (registered trademark) 2000 (GE Healthcare Japan Corporation). In an exemplary method, the test antibody is immobilized on a surface of a sensor chip and a fusion protein of human TSLP receptor and mouse Fc (human TSLP receptor-mouse Fc fusion protein (being encoded by the base sequence of SEQ ID NO: 6)) is added to the flow path. It is possible to confirm whether the test antibody binds to human TSLP receptor by analyzing binding rate constant (ka), dissociation rate constant (kd), and dissociation constant (KD) between the antibody and human TSLP receptor.

Further, the antibody or the antigen-binding fragment thereof of the present invention includes an antibody or an antigen-binding fragment thereof binding to TSLP receptor derived from other animals (for example, monkey TSLP receptor) and binding activity with respect to the receptors can be measured using the same method.

Preferably, the anti-human TSLP receptor antibody or the antigen-binding fragment thereof of the present invention binds to human TSLP receptor and has neutralizing activity with respect to human TSLP receptor. The neutralizing activity with respect to human TSLP receptor means activity of inhibiting any biological activity brought from human TSLP by binding to human TSLP receptor, and can be evaluated based on one or plural biological activities of human TSLP through human TSLP receptor as an index. Examples of such neutralizing activity include an inhibitory activity on TSLP-induced TARC mRNA expression and an inhibitory activity on TSLP-induced MDC protein production using human peripheral blood mononuclear cells (PBMC), and methods described in Examples 5 and 6 below can be used as a specific evaluation method of the activity.

For evaluating effects of the anti-human TSLP receptor antibody or the antigen-binding fragment thereof of the present invention in more detail, an in vivo test can be used. For example, as described in Example 7 below, it is possible to evaluate effects of the anti-human TSLP receptor antibody in vivo with an anti-allergic reaction test using a monkey *Ascaris* antigen sensitization model.

The anti-human TSLP receptor antibody or the antigen-binding fragment thereof of the invention can be easily produced by a person skilled in the art using a known method in the field based on sequence information on the heavy chain variable region and the light chain variable region of the anti-human TSLP receptor antibody of the invention which is disclosed in the present specification. The anti-human TSLP receptor antibody or the antigen-binding fragment thereof of the present invention is not particularly limited, but can be manufactured according to a method described in the section of <Method of producing anti-human TSLP receptor antibody of the invention> below.

The anti-human TSLP receptor antibody or the antigen-binding fragment thereof of the present invention is further purified as needed and formulated according to a conventional method. It may be used for the prevention or the treatment of diseases in which human TSLP and human TSLP receptor are involved with disease pathology, including allergic inflammatory diseases such as asthma, and systemic sclerosis.

A Polynucleotide of the Present Invention

A polynucleotide of the present invention includes a polynucleotide comprising a base sequence encoding the heavy chain variable region of the anti-human TSLP receptor antibody of the present invention and a polynucleotide comprising a base sequence encoding the light chain variable region of the anti-human TSLP receptor antibody of the present invention.

In one embodiment, the polynucleotide comprising a base sequence encoding the heavy chain variable region of the anti-human TSLP receptor antibody of the present invention is a polynucleotide comprising a base sequence encoding the heavy chain variable region consisting of the amino acid sequence of amino acid numbers 1 to 118 of SEQ ID NO: 1.

A polynucleotide comprising the base sequence encoding the heavy chain variable region shown by the amino acid sequence of amino acid numbers 1 to 118 of SEQ ID NO: 1 includes, for example, a polynucleotide comprising the base sequence from the base numbers 1 to 354 of SEQ ID NO:2.

In a preferred embodiment, the polynucleotide comprising the base sequence encoding the heavy chain variable region of the anti-human TSLP receptor antibody of the present invention is a polynucleotide comprising the base sequence encoding the heavy chain consisting of the amino acid sequence shown by SEQ ID NO: 1.

A polynucleotide comprising the base sequence encoding the heavy chain consisting of the amino acid sequence shown by SEQ ID NO: 1 includes, for example, a polynucleotide comprising the base sequence shown by SEQ ID NO: 2.

In one embodiment, the polynucleotide comprising the base sequence encoding the light chain variable region of the anti-human TSLP receptor antibody of the present invention is a polynucleotide comprising a base sequence encoding the light chain variable region consisting of the amino acid sequence of amino acid numbers 1 to 108 of SEQ ID NO: 3.

A polynucleotide comprising the base sequence encoding the light chain variable region consisting of the amino acid sequence of amino acid numbers 1 to 108 of SEQ ID NO: 3 includes, for example, a polynucleotide comprising the base sequence from the base numbers 1 to 324 of SEQ ID NO: 4.

In a preferred embodiment, the polynucleotide comprising the base sequence encoding the light chain variable region of the anti-human TSLP receptor antibody of the present invention is a polynucleotide comprising a base sequence encoding the light chain consisting of the amino acid sequence shown by SEQ ID NO: 3.

A polynucleotide comprising the base sequence encoding the light chain consisting of the amino acid sequence shown by SEQ ID NO: 3 includes, for example, a polynucleotide comprising the base sequence shown by SEQ ID NO: 4.

The polynucleotide of the present invention can be easily produced by a person skilled in the art using a known method in the field based on the base sequence. For example, the polynucleotide of the present invention can be synthesized using a known gene synthesis method in the field. A gene synthesis method includes, for example, various methods known by a person in the art such as a synthesis method of antibody genes disclosed in WO90/07861.

Expression Vector of the Present Invention, Transformed Host Cell of the Present Invention, Method of Producing Anti-Human TSLP Receptor Antibody of the Present Invention, and Anti-Human TSLP Receptor Antibody Produced by the Method An expression vector of the present invention includes an expression vector comprising the polynucleotide comprising the base sequence encoding the heavy chain variable region of the anti-human TSLP receptor antibody of the present invention and/or the polynucleotide comprising the base sequence encoding the light chain variable region of the anti-human TSLP receptor antibody of the present invention.

Preferred expression vectors of the present invention include an expression vector comprising a polynucleotide comprising the base sequence encoding the heavy chain of the anti-human TSLP receptor antibody of the present invention, an expression vector comprising a polynucleotide comprising the base sequence encoding the light chain of the anti-human TSLP receptor antibody of the present invention, or an expression vector comprising a polynucleotide comprising the base sequence encoding the heavy chain of the anti-human TSLP receptor antibody of the present invention and a polynucleotide comprising the base sequence encoding the light chain of the antibody.

The expression vector used to express the polynucleotide of the present invention are not particularly limited as long as a polynucleotide comprising the base sequence encoding the heavy chain variable region of the anti-human TSLP receptor antibody of the present invention and/or a polynucleotide comprising the base sequence encoding the light chain variable region of the anti-human TSLP receptor antibody of the present invention can be expressed in various host cells of eukaryotic cells (for example, animal cells, insect cells, plant cells, and yeast) and/or prokaryotic cells (for example, *Escherichia coli*), and the polypeptides encoded by these can be produced. Examples of the expression vector include plasmid vectors, viral vectors (for example, adenovirus or retrovirus), and the like. Preferably pEE6.4 or pEE12.4 (Lonza, Inc.) can be used. Further, antibody genes can be expressed by transferring a variable region gene fragment to expression vectors comprising human Ig constant region genes in advance such as AG-γ1 or AG-κ (for example, see WO94/20632).

The expression vector of the present invention may include a promoter that is operably linked to the polynucleotide of the present invention. Examples of the promoter for expressing the polynucleotide of the invention with animal cells include a virus-derived promoter such as CMV, RSV, or SV40, an actin promoter, an EF (elongation factor) 1α promoter, and a heat shock promoter. Examples of promoters for expression by bacteria (for example, *Escherichia*) include a trp promoter, a lac promoter, λPL promoter, and tac promoter. Further, examples of promoters for expression by yeast include a GAL1 promoter, a GAL10 promoter, a PH05 promoter, a PGK promoter, a GAP promoter, and an ADH promoter.

The transformed host cell of the present invention includes a host cell transformed with the expression vector of the present invention which is selected from the group consisting of the following (a) to (d):

(a) a host cell transformed with an expression vector comprising the polynucleotide comprising the base sequence encoding the heavy chain variable region of the anti-human TSLP receptor antibody of the present invention and the polynucleotide comprising the base sequence encoding the light chain variable region of the antibody;

(b) a host cell transformed with an expression vector comprising the polynucleotide comprising the base sequence encoding the heavy chain variable region of the anti-human TSLP receptor antibody of the present invention and an expression vector comprising the polynucleotide comprising the base sequence encoding the light chain variable region of the antibody;

(c) a host cell transformed with an expression vector comprising the polynucleotide comprising the base sequence encoding the heavy chain variable region of the anti-human TSLP receptor antibody of the present invention; and (d) a host cell transformed with an expression vector comprising the polynucleotide comprising the base sequence encoding the light chain variable region of the anti-human TSLP receptor antibody of the present invention.

In one embodiment, the transformed host cell of the present invention is a host cell transformed with the expression vector of the present invention which is selected from the group consisting of the following (a) to (d):

(a) a host cell transformed with an expression vector comprising a polynucleotide comprising the base sequence encoding the heavy chain of the anti-human TSLP receptor antibody of the present invention and a polynucleotide comprising the base sequence encoding the light chain of the antibody;

(b) a host cell transformed with an expression vector comprising a polynucleotide comprising the base sequence encoding the heavy chain of the anti-human TSLP receptor antibody of the present invention and an expression vector comprising a polynucleotide comprising the base sequence encoding the light chain of the antibody;

(c) a host cell transformed with an expression vector comprising a polynucleotide comprising the base sequence encoding the heavy chain of the anti-human TSLP receptor antibody of the present invention; and (d) a host cell transformed with an expression vector comprising a polynucleotide comprising the base sequence encoding the light chain of the anti-human TSLP receptor antibody of the present invention.

In the case of using an animal cell, an insect cell, or yeast as the host cell, the expression vector of the present invention may comprise initiation codon and termination codon. In this case, the expression vector of the present invention may comprise an enhancer sequence, an untranslated region on the 5' side and the 3' side of genes encoding the antibody of the present invention or the heavy chain variable region or the light chain variable region, a secretory signal sequence, a splicing junction, a polyadenylation site, or a replicable unit. When *Escherichia coli* is used as the host cell, the expression vector of the present invention may comprise an initiation codon, a termination codon, a terminator region, and a replicable unit. In this case, the expression vector of the present invention may comprise a selection marker (for example, tetracycline resistant genes, ampicillin resistant genes, kanamycin resistant genes, neomycin resistant genes, or dihydrofolate reductase genes) which is generally used according to the necessity.

Preferred examples of the transformed host cell of the present invention include a host cell transformed with an expression vector comprising a polynucleotide comprising the base sequence encoding the heavy chain of the anti-human TSLP receptor antibody of the present invention and a polynucleotide comprising the base sequence encoding the light chain of the antibody, and a host cell transformed with an expression vector comprising a polynucleotide comprising the base sequence encoding the heavy chain of the anti-human TSLP receptor antibody of the present invention and an expression vector comprising a polynucleotide comprising the base sequence encoding the light chain of the antibody.

The transformed host cell is not particularly limited as long as the host cell is appropriate for the expression vector being used, transformed with the expression vector, and can express the antibody. Examples of the transformed host cell include various cells such as natural cells or artificially established cells which are generally used in the field of the present invention (for example, animal cells (for example, CHO-K1SV cells), insect cells (for example, Sf9), bacteria (for example, *Escherichia*), yeast (for example, *Saccharomyces* or *Pichia*) or the like). Preferably cultured cells such as CHO-K1SV cells, CHO-DG 44 cells, 293 cells, or NSO cells can be used.

A method of transforming the host cell is not particularly limited, but, for example, a calcium phosphate method or an electroporation method can be used.

Methods of producing the anti-human TSLP receptor antibody or the antigen-binding fragment thereof of the present invention include a method of producing the anti-human TSLP receptor antibody or the antigen-binding fragment thereof which comprises culturing the transformed host cell of the present invention to express the anti-human TSLP receptor antibody or the antigen-binding fragment thereof.

The anti-human TSLP receptor antibody or the antigen-binding fragment thereof of the present invention include an anti-human TSLP receptor antibody or the antigen-binding fragment thereof produced by the method of producing the anti-human TSLP receptor antibody or the antigen-binding fragment thereof of the present invention.

The method of producing the anti-human TSLP receptor antibody or the antigen-binding fragment thereof of the present invention is not particularly limited as long as the method comprises culturing the transformed host cell of the present invention to express the anti-human TSLP receptor antibody or the antigen-binding fragment thereof. The preferable host cell used in the method includes the transformed host cell of the present invention which is described above as a preferred example.

The transformed host cell can be cultured by known methods. Culture conditions, for example, the temperature, pH of culture medium, and the culture time are appropriately selected. In a case where the host cell is an animal cell, examples of the culture medium include MEM culture medium supplemented with approximately 5% to 20% of fetal bovine serum (Science, 1959, Vol. 130, No. 3373, p. 432 to 7), DMEM culture medium (Virology, 1959, Vol. 8, p. 396), and RPMI1640 culture medium (J. Am. Med. Assoc., 1967, Vol. 199, p. 519), a 199 culture medium (Exp. Biol. Med., 1950, Vol. 73, p. 1 to 8). The pH of the culture medium is preferably approximately 6 to 8, and the culture is generally carried out at approximately 30° C. to 40° C. for approximately 15 hours to 72 hours while air ventilating and stirring if necessary. In a case where the host cell is an insect cell, as the culture medium, for example, Grace's culture medium (Proc. Natl. Acad. Sci. USA, 1985, Vol. 82, p. 8404) supplemented with fetal bovine serum can be used. The pH of the culture medium is preferably approximately 5 to 8, and the culture is generally carried out at approximately 20° C. to 40° C. for approximately 15 hours to 100 hours while air ventilating and stirring if necessary. In a case where the host cell is *Escherichia coli* or yeast, as the culture medium, for example, liquid culture medium supplemented with a source of nutrients is appropriate. It is preferable that the nutrient culture medium include a carbon source, an inorganic nitrogen source, or an organic nitrogen source necessary for the growth of the transformed host cell. Examples of the carbon source include glucose, dextran, soluble starch, and sucrose and examples of the inorganic nitrogen source or the organic nitrogen source include ammonium salts, nitrate salts, amino acids, corn steep liquor, peptone, casein, meat extract, soybean meal, and potato extract. Other nutrients (for example, inorganic salts (for example, calcium chloride, sodium dihydrogen phosphate, and magnesium chloride), vitamins), and antibiotics (for example, tetracycline, neomycin, ampicillin, and kanamycin) may be included as desired. The pH of the culture medium is preferably approximately 5 to 8. In a case where the host cell is *Escherichia coli*, preferred examples of the culture medium include LB culture medium and M9 culture medium (Mol. Clo., Cold Spring Harbor Laboratory, Vol. 3, A2.2). The culture is generally carried out at approximately 14° C. to 43° C. for approximately 3 hours to 24 hours while air ventilating and stirring if necessary. In a case where the host cell is yeast, as the culture medium, for example, Burkholder minimal medium (Proc. Natl. Acad, Sci, USA, 1980, Vol. 77, p. 4505) can be used. The culture is generally carried out at approximately 20° C. to 35° C. for approximately 14 hours to 144 hours while air ventilating and stirring if necessary. By carrying out the culture in the above-described manner, it is possible to express the anti-human TSLP receptor antibody or the antigen-binding fragment thereof of the present invention.

The method of producing the anti-human TSLP receptor antibody or the antigen-binding fragment thereof of the present invention may include recovering, preferably isolating or purifying the anti-human TSLP receptor antibody or the antigen-binding fragment thereof from the transformed host cell in addition to culturing the transformed host cell of the present invention to express the anti-human TSLP receptor antibody or the antigen-binding fragment thereof. Examples of the isolation or purification method include methods using solubility such as salting-out and the solvent precipitation method, methods using the difference in molecular weight such as dialysis, ultrafiltration, and gel filtration, methods using an electric charge such as ion exchange chromatography and hydroxylapatite chromatography, methods using specific affinity such as affinity chromatography, methods using the difference in hydrophobicity such as reverse phase high performance liquid chromatography, and methods using the difference in the isoelectric point such as isoelectric focusing phoresis. Preferably, the antibody accumulated in a culture supernatant can be purified by various chromatographies, for example, column chromatography using Protein A column or Protein G column.

Pharmaceutical Composition of the Present Invention

The pharmaceutical compositions of the present invention include a pharmaceutical composition comprising the anti-human TSLP receptor antibody or the antigen-binding fragment thereof of the present invention and pharmaceutically acceptable excipients. The pharmaceutical composition of the present invention can be prepared by a method being generally used with excipients, that is, excipients for medicine or carriers for medicine being generally used in the field. Examples of dosage forms of the pharmaceutical compositions include parenteral drug such as an injection drug and a drip infusion drug, and these can be administered by intravenous administration, subcutaneous administration, or the like. In drug preparation, excipients, carriers, and additives in accordance with the dosage forms can be used within the pharmaceutically acceptable range.

The pharmaceutical compositions of the present invention may include plural kinds of anti-human TSLP receptor antibodies or antigen-binding fragments thereof of the present invention. For example, the present invention includes a pharmaceutical composition comprising an antibody in which lysine of the C terminal of the heavy chain is deleted, an antibody or an antigen-binding fragment thereof with post-translational modification to N terminal, an antibody in which lysine of the C terminal of the heavy chain is deleted and post-translation modification to N terminal is made, and/or an antibody which has lysine of the C terminal of the heavy chain and does not have post-translational modification to N terminal.

For example, the pharmaceutical composition of the present invention comprising the anti-human TSLP receptor antibody of the present invention includes a pharmaceutical composition comprising two or more kinds of the anti-human TSLP receptor antibodies among (1) to (4) below.

(1) The anti-human TSLP receptor antibody, comprising the heavy chain consisting of the amino acid sequence of amino acid numbers 1 to 447 of SEQ ID NO: 1, and the light chain consisting of the amino acid sequence shown by SEQ ID NO: 3.

(2) The anti-human TSLP receptor antibody, comprising the heavy chain which is consisting of the amino acid sequence shown by SEQ ID NO: 1 in which glutamic acid of the amino acid number 1 is modified by pyroglutamic acid and the light chain consisting of the amino acid sequence shown by SEQ ID NO. 3.

(3) The anti-human TSLP receptor antibody, comprising the heavy chain which is consisting of the amino acid sequence of amino acid numbers 1 to 447 of SEQ ID NO: 1 in which glutamic acid of the amino acid number 1 is modified by pyroglutamic acid and the light chain consisting of the amino acid sequence shown by SEQ ID NO. 3.

(4) The anti-human TSLP receptor antibody, comprising the heavy chain consisting of the amino acid sequence shown by SEQ ID NO: 1 and the light chain consisting of the amino acid sequence shown by SEQ ID NO. 3.

The addition amount of the anti-human TSLP receptor antibody or the antigen-binding fragment thereof of the present invention in drug preparation varies depending on the degree of a patient's symptoms, the age of a patient, dosage form of the drug to be used, the binding titer of the antibody, or the like, and for example, an addition amount of approximately 0.001 mg/kg to 100 mg/kg can be used.

The pharmaceutical composition of the present invention can be used as a pharmaceutical composition for preventing or treating diseases in which human TSLP and human TSLP receptor are involved in disease pathology, such as asthma.

The present invention includes a pharmaceutical composition for preventing or treating asthma comprising the anti-human TSLP receptor antibody or the antigen-binding fragment thereof of the present invention. Further, the present invention includes a method for preventing or treating asthma, comprising administering a therapeutically effective amount of the anti-human TSLP receptor antibody or the antigen-binding fragment thereof of the present invention. In addition, the present invention includes an anti-human TSLP receptor antibody or an antigen-binding fragment thereof of the present invention, for use in preventing or treating asthma. In addition, the present invention includes use of the anti-human TSLP receptor antibody or the antigen-binding fragment thereof of the present invention for the manufacture of a pharmaceutical composition for preventing or treating asthma.

The present invention has been generally described and specific examples referred to for better understanding will be provided, but these are merely examples and the present invention is not limited thereto.

EXAMPLES

With regard to parts using commercially available kits or reagents, the tests are performed according to the attached protocol unless otherwise noted. Further, for convenience, concentration mol/L is expressed as M. For example, a 1 M aqueous sodium hydroxide solution means 1 mol/L of an aqueous sodium hydroxide solution.

Example 1

Acquisition of TSLP Receptor-Fc Fusion Protein

For evaluation of binding activity of an antibody, a fusion protein of human TSLP receptor and human Fc (human TSLP receptor-humans Fc fusion protein), a fusion protein of human TSLP receptor and mouse Fc (human TSLP receptor-mouse Fc fusion protein), and a fusion protein of monkey TSLP receptor and human Fc (monkey TSLP receptor-human Fc fusion protein) were obtained. The human TSLP receptor-human Fc fusion gene (SEQ ID NO: 5), the human TSLP receptor-mouse Fc fusion gene (SEQ ID NO: 6), and the monkey TSLP receptor-human Fc fusion gene (SEQ ID NO: 7) were respectively recombined with mammal cell expression vectors, GS vectors (Lonza, Inc.) pEE12.4. The prepared vectors were gene-transferred to FreeStyle 293 cells (Life technologies, Inc) using a gene transfer reagent 293 fectin (Life technologies, Inc), and the cells were cultured by a serum-free culture system using FreeStyle 293 Expression medium (Life technologies, Inc) for one week, and then culture supernatants comprising the human TSLP receptor-human Fc fusion protein, the human TSLP receptor-mouse Fc fusion protein, and the monkey TSLP receptor-human Fc fusion protein were respectively obtained. Respective TSLP receptor-Fc fusion proteins were purified using a protein purification column Protein G column (GE Healthcare Japan Corporation) from the obtained culture supernatants.

Example 2

Acquisition of TSLP Mutant-Flag Proteins

For evaluation of neutralizing activity of an antibody, a human TSLP mutant protein with Flag tag (human TSLP mutant-Flag protein) and a monkey TSLP mutant protein with Flag tag (monkey TSLP mutant-Flag protein) were obtained. Human or monkey TSLP mutant-Flag gene (SEQ ID NO: 8 or 9 (in order to prevent for activity from being lost by being cut through furin protease, amino acid sequences of human or monkey wild type TSLP in which mutation is inserted into the cut site were encoded respectively) were respectively recombined with GS vectors pEE12.4. The prepared vectors were gene-transferred to FreeStyle 293 cells using a 293 fectin, and the cells were cultured by a serum-free culture system using FreeStyle 293 Expression medium for one week, and then culture supernatants comprising the human TSLP mutant-Flag proteins or the monkey TSLP mutant-Flag proteins were respectively obtained. Respective TSLP mutant-Flag proteins were purified using an anti-FLAG M2 antibody affinity gel (Sigma, Inc.) from the obtained culture supernatants.

Example 3

Preparation of Fully Human Anti-Human TSLP Receptor Antibody

A human monoclonal antibody development technology "VelocImmune" (VelocImmune antibody technology: Regeneron, Inc. (U.S. Pat. No. 6,596,541) mouse was immunized by an adjuvant for causing an immune reaction, human TSLP receptor-Fc (R&D, Inc.), and human TSLP receptor expressing Ba/F3 cells (prepared by transferring vectors encoding human TSLP receptor genes (SEQ ID NO: 10) and human IL-7 receptor α chain genes (SEQ ID NO:11) to mouse Ba/F3 cells (RIKEN: RCB0805)). According to the conventional method, a spleen or a lymph node of the immunized mouse was extracted, lymphocytes were collected, and cell-fused with mouse myeloma cells SP2/0 CC CRL-1581), thereby preparing hybridoma. The hybridoma was monocloned, and then cultured in a CD hybridoma culture medium (Life technologies, Inc.) which is a serum-free medium. The antibody was purified using an antibody purification kit Protein G Purification kit (Proteus, Inc.) from the obtained culture supernatants.

For evaluation of binding activity of the antibody, ELISA using the human TSLP receptor-human Fc fusion protein and the monkey TSLP receptor-human Fc fusion protein prepared in Example 1 was respectively performed. Further, for evaluation of neutralizing activity of the antibody, a cell growth inhibition assay of human TSLP receptor expressing Ba/F3 cells by stimulation of the monkey TSLP mutant-Flag proteins prepared in Example 2 and an MDC protein production inhibition assay on monkey whole blood by stimulation of the monkey TSLP mutant-Flag proteins prepared in Example 2 were performed.

From the above-described tests, it was revealed that the antibody (chimeric antibody) referred to as T7-27 had binding activity and neutralizing activity with respect to human and monkey TSLP receptors. Genes encoding the heavy chain and the light chain of the antibody from hybridoma producing T7-27 were cloned and a sequence determination was made.

In the above-described antibody, the variable region is human-derived and the constant region is mouse-derived. For this reason, expression vectors comprising both genes of the heavy chain and the light chain were constructed using GS vectors and a fully human antibody was prepared. Specifically, genes encoding signal sequences (Nigel Whittle et al., Protein Engineering 1987; 1(6): 499 to 505.) were connected to the 5' side of heavy chain variable region genes of the antibody of T7-27 and constant region genes (consisting of the base sequence of base numbers 355 to 1344 of SEQ ID NO: 2) of human Igγ1 were connected to the 3' side thereof, and then the heavy chain genes were inserted to GS vector pEE6.4. Further, genes encoding signal sequences (Nigel Whittle et al., mentioned above) were connected to the 5' side of light chain variable region genes of the antibody and constant region genes (consisting of the base sequence of base numbers 325 to 642 of SEQ ID NO: 4) of human Igκ were connected to the 3' side thereof, and then the light chain genes were inserted into GS vector pEE12.4.

The base sequence encoding the heavy chain of the fully human antibody of the prepared T7-27 (fully human T7-27) is shown by SEQ ID NO: 2, the amino acid sequence encoded by that is shown by SEQ ID NO: 1, and the base sequence encoding the light chain of the antibody is shown by SEQ ID NO: 4, and the amino acid sequence encoded by that is shown by SEQ ID NO: 3. The heavy chain variable region of the fully human T7-27 consists of the amino acid sequence of amino acid numbers 1 to 118 of SEQ ID NO: 1, and CDR1, CDR2, and CDR 3 of the heavy chain respectively consist of the amino acid sequence of amino acid numbers 31 to 35, 50 to 66, and 99 to 107 of SEQ ID NO: 1. The light chain variable region of the fully human T7-27 consists of the amino acid sequence of amino acid numbers 1 to 108 of SEQ ID NO: 3, and CDR1, CDR2, and CDR 3 of the light chain respectively consist of the amino acid sequence of amino acid numbers 24 to 34, 50 to 56, and 89 to 97 of SEQ ID NO: 3.

The antibody was expressed using two kinds of methods of transient expression and constitutive expression with the above-described GS vectors to which genes of the heavy chain and the light chain of the antibody were respectively inserted. With regard to the transient expression, the expression vectors of both the heavy chain and the light chain were transfected using the 293 fectin with respect to FreeStyle 293 cells cultured in approximately 1,000,000 cells/mL in a FreeStyle 293 Expression medium, and then cultured for 7 days. Alternatively, the expression vectors of both of the heavy chain and the light chain described above were transfected using an electroporation method with respect to approximately 10,000,000 CHO-K1SV cells (Lonza, Inc.), and then cultured in a CD-CHO medium (Life technologies, Inc.) for 7 days. The culture supernatants were purified using Protein A column or Protein G column (GE Healthcare Japan Corporation) and a purified antibody of the fully human antibody was obtained. With regard to the constitutive expression, the GS vectors to which genes of the heavy chain and the light chain of the antibody were respectively inserted were cut with a restriction enzyme by NotI and PvuI, and ligation was performed using a kit Ligation-Convenience Kit for ligation (NIPPONGENE, Inc.) or a ligation reagent Ligation-high (TOYOBO, Inc.), and then the GS vectors to which both genes of the heavy chain and the light chain were inserted were constructed. The expression vectors encoded the full length of the heavy chain and the light chain, and the antibody was expressed by transfection in CHO-K1SV cells. The culture supernatants were purified with Protein A column or Protein G column (GE Healthcare Japan Corporation) and a purified antibody of the fully human antibody was obtained. As a result of analyzing amino acid modification of the purified fully human T7-27, deletion of lysine of the heavy chain C terminal occurred in a large part of the purified antibody.

Example 4

Evaluation on Binding Activity by SPR Analysis

For measuring binding activity of the fully human T7-27 in detail, SPR analysis was performed. In the present example, an anti-human TSLP receptor antibody TSLPR-012_141 (Patent Document 4) was used as a comparative antibody.

In the SPR analysis, the analysis was performed using Biacore (registered trademark) 2000 (GE Healthcare Japan Corporation). Respective anti-human TSLP receptor antibodies were immobilized on the surface of a sensor chip CM5 using a Human Antibody Capture Kit and an Amine Coupling Kit (GE Healthcare Japan Corporation). The human TSLP receptor-mouse Fc fusion protein obtained in Example 1 was serially diluted with an HBS-EP solution (GE Healthcare Japan Corporation), and 100 μL of the solution was added to the flow path at a flow rate of 50 μL/min. By this measurement system, binding rate constant (ka), dissociation rate constant (kd), and dissociation constant (KD) of the human TSLP receptor-mouse Fc fusion protein and the anti-human TSLP receptor antibody were calculated using data analysis software (BIA Evaluation) (Table 1).

TABLE 1

| Binding activity with respect to human TSLP receptor by SPR analysis | | |
|---|---|---|
| | KD (M) | Kd (1/s) |
| Fully human T7-27 | $0.41 \times 10^{-8}$ | $1.25 \times 10^{-4}$ |
| TSLPR-012_141 | $1.26 \times 10^{-8}$ | $3.38 \times 10^{-4}$ |

As a result, it became clear that the fully human T7-27 had approximately 3 fold stronger binding activity compared to TSLPR-012_141.

Example 5

Evaluation of TSLP-Induced TARC mRNA Expression Inhibition Using Human PBMC

For evaluation of the neutralizing activity of the fully human T7-27, TSLP-induced TARC mRNA expression inhibition in the human peripheral blood mononuclear cells (PBMC) was evaluated. Since the human PBMC include dendritic cells expressing TSLP receptor, the human PBMC can be used for evaluation of the anti-human TSLP receptor antibody. As a comparative antibody, TSLPR-012_141 was used. From the result of Test Example 1 described below, since a correlation between pathology improvement of an asthma model and inhibition of blood TARC mRNA expression using the anti-TSLP receptor antibody was found, the present evaluation system is an evaluation system indicating effectiveness on pathology.

200,000 cells of human PBMC (AllCells, Inc.) per well in 96 well plates (Gleiner, Inc.) were seeded at 160 μL of a PRMI1640 culture medium (Life technologies, Inc.). A dilution series (7 steps of the final concentration in the range of 0.1 ng/mL to 100 ng/mL) of the human TSLP mutant—Flag proteins prepared in Example 2 was prepared in the RPMI164 culture medium and 20 μL thereof were added to the culture solution, followed by incubation for 24 hours in a CO$_2$ incubator whose temperature was set to 37° C. Then, respective anti-human TSLP receptor antibodies were prepared in the RPMI1640 medium such that the final concentration became 0.3 μg/mL, and added to the culture solution in an amount of 20 μL, and further incubated for 72 hours. As a control sample, a well to which the RPMI1640 culture medium was added instead of the human TSLP mutant-Flag proteins and a well to which the RPMI1640 culture medium was added instead of the antibody were respectively prepared. 200 μL of culture supernatants were removed, and then total RNA was extracted with 30 μL of water using a kit RNeasy 96 kit (Qiagen, Inc.) for RNA purification. Subsequently, 10 μL of RNA was subjected to a reverse transcription reaction using a kit for reverse transcription, High Capacity cDNA Reverse Transcription Kit (Life technologies, Inc.). Next, the expression level of TARC mRNA was measured by a TaqMan PCR method using a TaqMan probe of TARC (Cell7, Hs00171074, Life technologies, Inc), a TaqMan probe of β actin (Actb, Hs99999903, Life technologies, Inc.), Express qPCR SuperMix (A10313, Life technologies, Inc.) and 2 μL of cDNA. The test was duplicated for respective antibodies, and the measurement result was analyzed using a comparison CT method, and then the expression level of TARC mRNA was calculated. Subsequently, an inhibition rate of the antibody in each TSLP concentration was calculated. The inhibition rate of a well to which the RPMI1640 culture medium was added instead of the human TSLP mutant-Flag proteins was set to 100% and the average value of a well to which 30 ng/ml and 100 ng/ml of the human TSLP mutant-Flag proteins were respectively added was set as the inhibition rate of 0%. The calculated inhibition rate was analyzed, and the TSLP concentration having 50% of the inhibition rate of a 0.3 μg/mL antibody was calculated (Table 2) by fitting a three parameter logistic curve. As this TSLP concentration becomes higher, the neutralizing activity with respect to TSLP of the test antibody becomes stronger.

TABLE 2

| TSLP-induced TARC mRNA expression inhibition activity using human PBMC | |
|---|---|
| | TSLP concentration (ng/mL) |
| Fully human T7-27 | 1.25 |
| TSLPR-012_141 | 0.08 |

As a result, it became clear that the fully human T7-27 had approximately 12 fold higher inhibition activity against human TSLP-induced TARC mRNA expression compared to the TSLPR-012_141.

Example 6

Evaluation of TSLP-Induced MDC Proteins Production Inhibition Using Human PBMC The TSLP-induced MDC proteins production inhibition in the human PBMC was evaluated for evaluation of the neutralizing activity of the fully human T7-27. As a comparative antibody, TSLPR-012_141 was used.

Human blood was diluted in the same amount of PBS, and laminated on the same amount of Ficoll-Paque PLUS (GE Healthcare Japan Corporation), and then subjected to a centrifugal treatment under the conditions of room temperature, 400×g, and for 30 minutes, thereby preparing the human PBMC. Approximately 300,000 cells of human PBMC per well in 96 well plates (Gleiner, Inc.) were seeded at 100 μL of a PRMI1640 culture medium (Life technologies, Inc.). The human TSLP mutant-Flag protein prepared in Example 2 was prepared in the RPMI1640 culture medium such that the final concentration thereof became 5 ng/mL, and added to the culture solution by an amount of 10 μL thereof, followed by incubation for 24 hours in a $CO_2$ incubator whose temperature was set to 37° C. Then, dilution series (5 steps of the final concentration in the range of 0.1 ng/mL to 10 μg/mL) of the respective anti-human TSLP receptor antibody was prepared at the RPMI164 culture medium and 10 μL thereof were added to the culture solution, followed by incubation for 5 days. As a control sample, a well to which the RPMI1640 culture medium was added instead of the human TSLP mutant-Flag proteins and a well to which the RPMI1640 culture medium was added instead of the antibodies were respectively prepared. Subsequently, the culture supernatants were collected and the production amount of MDC was evaluated using a Human CCL22/MDC Quantikine ELISA Kit (R&D, Inc.) with supernatants diluted by 20 fold by PBS (Life technologies, Inc.). The test was duplicated for respective antibodies, and the inhibition rate in each antibody concentration was calculated. The inhibition rate of a well to which the RPMI1640 culture medium was added instead of the human TSLP mutant-Flag proteins was set to 100% and the inhibition rate of a well to which the RPMI1640 culture medium was added instead of the antibody was set to 0%. The antibody concentration having 50% of the inhibition rate was calculated as IC 50 (Table 3) by fitting a three parameter logistic curve.

TABLE 3

Evaluation of TSLP-induced MDC proteins production inhibition using human PBMC

|  | IC50 (ng/mL) |
| --- | --- |
| Fully human T7-27 | 0.12 |
| TSLPR-012_141 | 1.10 |

As a result, it became clear that the fully human T7-27 had approximately 9 fold higher inhibition activity against TSLP-induced MDC proteins production compared to the TSLPR-012_141.

Example 7

Evaluation of Fully Human T7-27 in Monkey Ascaris Antigen Sensitization Model

Ascaris antigen specific IgE is induced by allowing a monkey to be sensitized with Ascaris antigen, and a skin reaction is caused as an allergic reaction.

An Ascaris antigen liquid (DNP-Ascaris (LSL, Inc.)) suspended by aluminum peroxide gel (hereinafter, referred to as Alum) (0.5 mg/mL DNP-Ascaris suspended in PBS at a concentration of 50 mg/mL Alum, hereinafter, referred to as Ascaris antigen-Alum liquid) was administered on Day 1, Day 8, and Day 15 to a male cynomolgus monkey in an amount of 3.6 mL/kg intraperitoneally and an amount of 0.4 mL/kg intramuscularly for sensitization. Further, as for treated groups, a Normal group (non-treated group, n=2), a Vehicle group (a group to which a solvent (20 mM sodium citrate buffer solution/120 mM NaCl (pH 6.0)) was administered intravenously before one day from sensitization, n=3) and an antibody administration group (a group to which 10 mg/kg of fully human T7-27 (dilution by a solvent) was administered intravenously before one day from sensitization, n=3) were respectively set.

In addition, Alum was prepared by the following method. Aluminum sulfate (14 to 18 hydrates) (Wako, Inc.) was dissolved in ultrapure water to prepare 1M solution, and the solution was filtered by a 0.22 μm filter, and then 1M sodium hydroxide (Nacalai Tesque) was added thereto until white precipitate was not generated. The supernatants were removed, washed by ultrapure water by 5 times, and then further washed by PBS (WAKO, Inc.) three times. The washed white precipitate was finely crushed by a homogenizer (CH-6010, KINEMATICA, Inc.) under ice, followed by centrifugation at 2000 rmp at a temperature of 4° C. for 5 minutes using a centrifuge (himac CR21, Hitachi, Ltd.). Then, the supernatants were removed, and washed with PBS twice. The obtained precipitate was suspended in PBS to obtain Alum.

Measurement of Plasma Ascaris Antigen Specific IgE

Blood was continuously collected from the above-described cynomolgus monkey on Day 1 (before administration of an Ascaris antigen-Alum liquid), Day 8, Day 15, and Day 22, and plasma was collected after centrifugation (1800×g, 4° C., 10 minutes). The concentration of the Ascaris antigen specific IgE in plasma was measured using the following method.

DNP-Ascaris was prepared by PBS such that the concentration thereof became 100 μg/mL, and added to a Nunc-Immuno™ Micro Well™ 96 well solid plate (Nunc Inc.) in an amount of 100 μL, and then immobilized at room temperature overnight. A blocking agent (Blocking One: Nacalai Tesque) was added thereto in an amount of 200 μL, and left for stand at room temperature for 30 minutes, and the solution was removed. Subsequently, the recovered plasma and a sample for a calibration curve were respectively added in an amount of 100 μL. As the sample of a calibration curve, the concentration of plasma Ascaris antigen specific IgE of one of the Vehicle group on Day 22 was set to 2000 U/mL and a dilution series (2000 mU/mL to 16 mU/mL) was prepared by a dilution solution (5% Blocking One containing PBS) and used. Incubation was performed at room temperature for 1 hour, followed by washing five times in T-PBS (0.05% Tween-20 containing PBS), and then an HRP labeled human IgE detection antibody (A80-108P: Bethyl, Inc.) diluted by 10000 fold in a dilution solution was added thereto in an amount of 100 μL. Further, incubation was performed at room temperature for 1 hour, followed by washing 5 times in T-PBS. Finally, measurement was carried out using a peroxidase color development kit (ML-1120T: SUMILON, Inc.). The absorbance was measured using SpectraMax (Molecular Devices, Inc.). The results of Day 1 and Day 22 are shown in FIG. 1.

Skin Test

Figure 2:
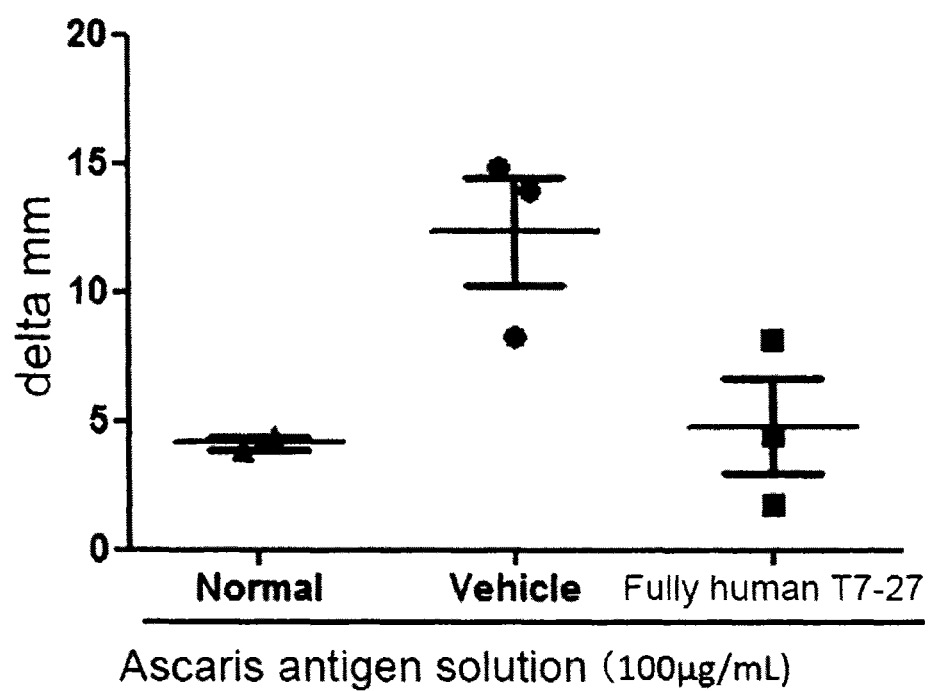
FIG. 2 shows an inhibitory action of fully human T7-27 on an *Ascaris* antigen-specific skin reaction in a monkey *Ascaris* antigen sensitization model. The results of administration of phosphate buffered saline (PBS) and 100 μg/mL *Ascaris* antigen solution on Day 22 are shown. The vertical axis represents a value (delta mm) in which a diameter of a skin reaction by PBS is subtracted from a diameter of a skin reaction by the *Ascaris* antigen solution.

On Day 22, PBS, 1, 10, and 100 μg/mL Ascaris antigen solution (a solution in which DNP-Ascaris is suspended by PBS) were intradermally administered at two places respectively (total 8 places per one animal) on the shaved abdomen of the same individual of the Vehicle group and the antibody administration group in an amount of 100 μL. With respect to the Normal group, PBS and 100 μg/mL Ascaris antigen solution were intradermally administered at 4 places respectively (total 8 places per one animal) on the shaved abdomen of the same individual in the amount of 100 μL. After 20 minutes of the skin sensitization, the skin reaction was observed by measuring the diameter using a Vernier caliper. In each individual, a value in which a diameter of the skin reaction by PBS administration was subtracted from a diameter of the skin reaction by the Ascaris antigen solution administration was set to delta mm. The results at 100 μg/mL Ascaris antigen solution are shown in FIG. 2. Further, in a case where 1 and 10 μg/mL *Ascaris* antigen solution was administered, a skin reaction sufficient for evaluating the test antibody was not generated.

The average value and the standard error of each group were acquired, and an inhibition rate was acquired by setting the value on Day 1 (value before administration of *Ascaris* antigen-Alum liquid) to 100% and the Vehicle group on Day 22 to 0% in measurement of the plasma *Ascaris* antigen specific IgE.

As shown in FIG. 1, the fully human T7-27 decreased (97% inhibition) the *Ascaris* antigen specific IgE concentration in the monkey *Ascaris* antigen sensitization model when compared to the Vehicle group.

As shown in FIG. 2, the fully human T7-27 decreased the *Ascaris* antigen specific skin reaction at 100 μg/mL *Ascaris* antigen solution in the monkey *Ascaris* antigen sensitization model when compared to the Vehicle group.

From the results described above, it became clear that the fully human T7-27 suppressed the allergic reaction caused by the *Ascaris* antigen specific IgE in the monkey *Ascaris* antigen sensitization model.

Test Example 1

Evaluation of Anti-TSLP Receptor Antibody in Mouse Mite Antigen Sensitization Asthma Model The mouse mite antigen sensitization model is known as an asthma model and the pathological conditions include increase in airway reactivity and infiltration of eosinophils to bronchoalveolar lavage.

Sensitization was performed by administering mite antigen (Dp) (LSL, Inc.) intraperitoneally to an NC/Nga mouse (Charles River, Inc.) with a dosage of 100 μg Dp/0.5 mL physiological saline/mouse on Day 0 (at the time of initial sensitization) and Day 5. The airway inflammation was caused by nasal administration of the mite antigen with a dosage of 100 μg Dp/50 μL physiological saline/mouse on Day 12 and Day 19. An anti-mouse TSLP receptor antibody (WAKO, Inc.) dissolved in PBS (WAKO, Inc.) was administered to the antibody administration group subcutaneously with a dosage (0.1, 1, 10 mg/kg) on Day −1, Day 2, Day 5, Day 8, Day 11, Day 14, and Day 18 (antibody administration day) once a day. A dexamethasone administration group (Dex group) was provided as a positive control group. The dexamethasone dissolved in PBS was administered to the Dex group intraperitoneally with a dosage of 3 mg/kg from Day 12 to Day 19 once a day. The set treated groups are as follows.

[Treated Groups]
Normal group (n=10):
Non-treated
Saline group (n=6):
The mite antigen was intraperitoneally administered on Day 0 and Day 5, physiological saline was nasally administered on Day 12 and Day 19, and PBS was subcutaneously administered at antibody administration day.
PBS group (n=10):
The mite antigen was intraperitoneally administered on Day 0 and Day 5, the mite antigen was nasally administered on Day 12 and Day 19, and PBS was subcutaneously administered at antibody administration day.
Antibody administration group (0.1, 1, 10 mg/kg) (n=10 for each dosage):
The mite antigen was intraperitoneally administered on Day 0 and Day 5, the mite antigen was nasally administered on Day 12 and Day 19, and the antibody was subcutaneously administered at antibody administration day.
Dex group (n=10):
The mite antigen was intraperitoneally administered on Day 0 and Day 5, the mite antigen was nasally administered on Day 12 and Day 19, and dexamethasone was intraperitoneally administered from Day 12 to Day 19.

Figure 3:
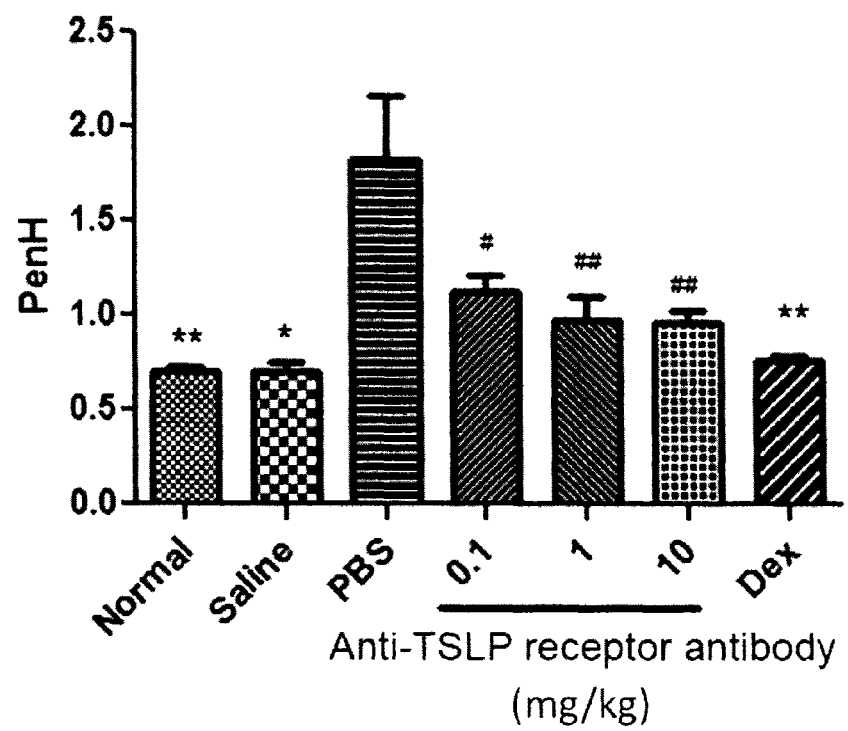
FIG. 3 shows an inhibitory action of an anti-TSLP receptor antibody on an airway hyperresponsiveness reaction in a mouse asthma model. The vertical axis represents a value of PenH used as an index of a respiratory function (**$p<0.01$, *$p<0.05$, ##$p<0.01$, #$p<0.05$).

A mouse was put in an unrestrained chamber exclusive for mice on Day 20. A transducer using a pneumotachograph was attached to the chamber, and was connected to a respiratory function analyzer BioSystem XA (Buxco, Inc.), and a change in pressure in the inside of the chamber with respect to atmospheric pressure was detected using the transducer. The concentration of Acetyl-β-methyl choline chloride (Sigma, Inc.) (0.25, 0.5, 1, 2, 4 mg/mL) dissolved in physiological saline was sequentially increased and then was subjected to inhalation exposure using an ultrasonic nebulizer for examining the airway reactivity. PenH mechanically calculated from the change in pressure in the inside of the chamber was used as an index of the respiratory function. The measurement results are shown in FIG. 3.

Figure 4:
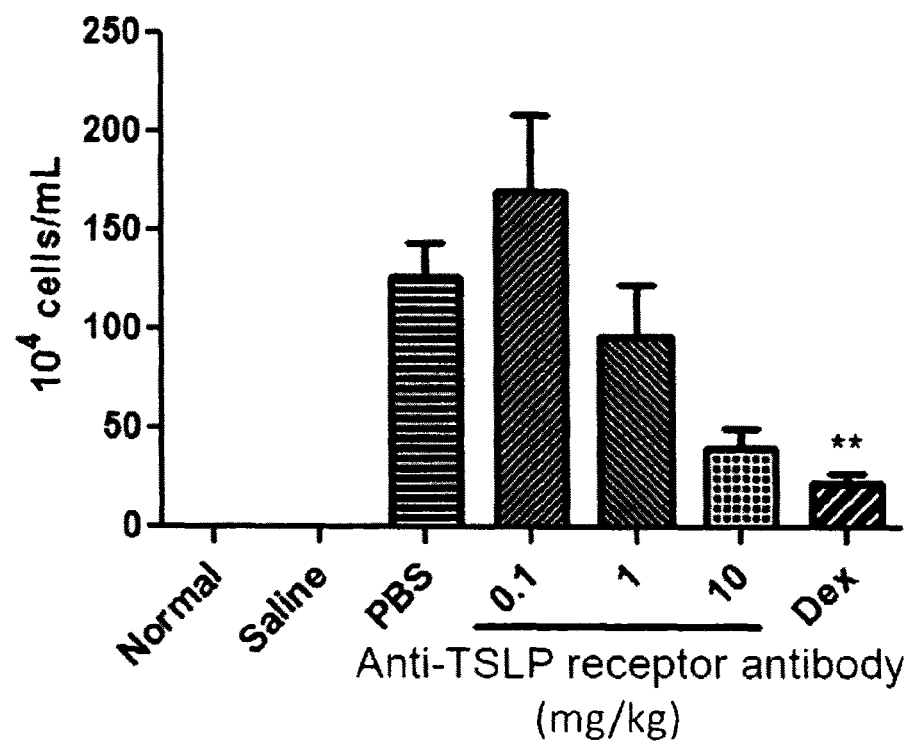
FIG. 4 shows an inhibitory action of the anti-TSLP receptor antibody on infiltration of eosinophils in the mouse asthma model. The vertical axis represents the number of eosinophils in a BALF cell suspension (**$p<0.01$).

Next, after blood of the mouse was collected from the vena cava of the abdomen, the mouse was euthanized by exsanguination. A cannula was intubated into the trachea, and the bronchoalveolar lavage was washed with 0.1% fetal bovine serum (BioWest, Inc.) containing PBS solution, and then the bronchoalveolar lavage fluid (BALF) was collected. The BALF was centrifuged, the supernatant was removed, the sediment was suspended in 500 μL of physiological saline, and a BALF cell suspension was prepared. The number of eosinophils in the BALF cell suspension was measured using a multi-item automatic blood cell analyzer XT-2000i (SYSMEX, Inc.). The measurement results are shown in FIG. 4.

Figure 5:
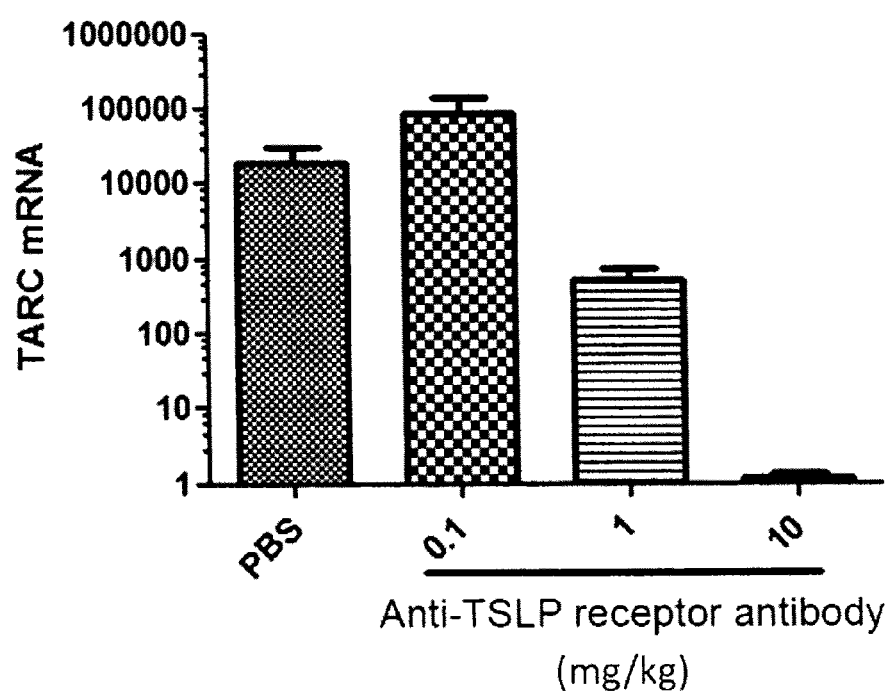
FIG. 5 shows an inhibitory action of the anti-TSLP receptor antibody on expression of TARC mRNA in the mouse asthma model. The vertical axis represents an expression level of TARC mRNA.

The obtained blood was diluted by 10 fold with RPMI1640 culture medium (Life technologies, Inc.). The diluted blood was seeded at 1 mL in a plate (IWAKI Co. Ltd.). Mouse TSLP (R&D, Inc.) was diluted by PBS such that the final concentration thereof became 0 or 10 ng/mL, and 100 μL thereof was added. Incubation was performed at 37° C. for 24 hours under 5% $CO_2$, and the total RNA was extracted with 30 μL of water using a RNeasy 96 Kit (Qiagen, Inc.). Next, 10 μL of RNA was subjected to a reverse transcription reaction using a High Capacity cDNA Reverse Transcription Kit (Life technologies, Inc.). Subsequently, the expression level of TARC mRNA was measured using a TaqMan PCR method using a TaqMan probe of TARC (Cell7, Mn01244826 g1, Life technologies, Inc.), a TaqMan probe of β-actin (Actb, Mm00607939 s1, Life technologies, Inc.), ExpressqPCR SuperMix (A10313, Life technologies, Inc.), and 2 μL of cDNA. The expression level was calculated by analyzing the measurement result using a comparison CT method. The results at 10 ng/mL TSLP are shown in FIG. 5.

The average values and standard errors of the respective groups were acquired. Student's-t test was used for a significant difference test between the PBS group and the Normal group, the Saline group, and the Dex group, respectively. For the significant difference test between the PBS group and the antibody administration group, multiple comparison of Dunnett was used. In both cases, significant differences were present in a case of $p<0.05$.

As shown in FIG. 3, in the antibody administration group, an inhibitory action on airway hyperresponsiveness induced by 1 mg/mL of acetyn-β-methyl choline chloride was found in the mouse asthma model compared to the PBS group. It became clear that the anti-TSLP receptor antibody improves the respiratory function in the asthma model.

As shown in FIG. 4, in the antibody administration group, the inhibitory action on infiltration of eosinophils into bronchoalveolar lavage was found compared to the PBS group.

As shown in FIG. 5, in the antibody administration group, the inhibitory action on expression of TARC mRNA was found compared to the PBS group.

It was confirmed that the anti-TSLP receptor antibody improved the pathological condition of the asthma model from the results of FIGS. 3 and 4. Further, a correlation between the improvement of the pathological condition and the inhibition of the TARC mRNA expression due to the anti-TSLP receptor antibody was found from the results of FIGS. 3 to 5 and it became clear that the improving effects on the pathological condition can be evaluated using the inhibitory effects on expression of the TARC mRNA as an index.

INDUSTRIAL APPLICABILITY

The anti-human TSLP receptor antibody of the present invention is useful for preventing and treating various diseases in which human TSLP and human TSLP receptor are involved in disease pathology. Further, the methods of producing the polynucleotide, the expression vectors, and the host cell of the present invention are useful for producing the anti-human TSLP receptor antibody.

SEQUENCE LIST FREE TEXT

In the number heading <223> of the sequence list, description of "Artificial Sequence" is made. Specifically, the base sequences shown by SEQ ID NO: 2 and SEQ ID NO: 4 of the sequence list is the base sequence of the heavy chain and the light chain of the fully human T7-27, respectively, and the amino acid sequences shown by SEQ ID NO: 1 and SEQ ID NO: 3 is the amino acid sequence of the heavy chain and the light chain encoded by the SEQ ID NO: 2 and SEQ ID NO: 4, respectively. The base sequences shown by SEQ ID NOS: 5, 6, 7, 8, and 9 of the sequence list is the base sequence encoding the human TSLP receptor-human Fc fusion protein, the human TSLP receptor-mouse Fc fusion protein, the monkey TSLP receptor-human Fc fusion protein, the human TSLP mutant-Flag protein, and the monkey TSLP mutant-Flag protein, respectively.

The invention claimed is:

1. A method for treating asthma, which comprises administering a therapeutically effective amount of an anti-human thymic stromal lymphopoietin (TSLP) receptor antibody or an antigen-binding fragment thereof, wherein the anti-human TSLP receptor antibody or the antigen-binding fragment thereof comprises a heavy chain variable region comprising CDR1 consisting of the amino acid sequence of amino acid numbers 31 to 35 of SEQ ID NO: 1, CDR2 consisting of the amino acid sequence of amino acid numbers 50 to 66 of SEQ ID NO: 1, and CDR3 consisting of the amino acid sequence of amino acid numbers 99 to 107 of SEQ ID NO: 1, and a light chain variable region comprising CDR1 consisting of the amino acid sequence of amino acid numbers 24 to 34 of SEQ ID NO: 3, CDR2 consisting of the amino acid sequence of amino acid numbers 50 to 56 of SEQ ID NO: 3, and CDR3 consisting of the amino acid sequence of amino acid numbers 89 to 97 of SEQ ID NO: 3.

2. The method for treating asthma according to claim 1, wherein the anti-human TSLP receptor antibody or the antigen-binding fragment thereof is selected from the group consisting of the following (1) and (2):

(1) an anti-human TSLP receptor antibody or an antigen-binding fragment thereof, comprising a heavy chain variable region consisting of the amino acid sequence of amino acid numbers 1 to 118 of SEQ ID NO: 1, and a light chain variable region consisting of the amino acid sequence of amino acid numbers 1 to 108 of SEQ ID NO: 3;

(2) an anti-human TSLP receptor antibody or an antigen-binding fragment thereof, wherein glutamic acid of the N-terminal of the heavy chain of the antibody or the antigen-binding fragment thereof of (1) is modified to pyroglutamic acid.

3. The method for treating asthma according to claim 2, wherein the anti-human TSLP receptor antibody or the antigen-binding fragment thereof comprises a heavy chain variable region consisting of the amino acid sequence of amino acid numbers 1 to 118 of SEQ ID NO: 1, and a light chain variable region consisting of the amino acid sequence of amino acid numbers 1 to 108 of SEQ ID NO: 3.

4. The method for treating asthma according to claim 2, wherein the anti-human TSLP receptor antibody or the antigen-binding fragment thereof is the anti-human TSLP receptor antibody or the antigen-binding fragment thereof comprising a heavy chain variable region consisting of the amino acid sequence of amino acid numbers 1 to 118 of SEQ ID NO: 1, and a light chain variable region consisting of the amino acid sequence of amino acid numbers 1 to 108 of SEQ ID NO: 3, wherein glutamic acid of the N-terminal of the heavy chain is modified to pyroglutamic acid.

5. The method for treating asthma according to claim 2, wherein the anti-human TSLP receptor antibody or the antigen-binding fragment thereof comprises a heavy chain constant region which is a human Igγ1 constant region.

6. The method for treating asthma according to claim 2, wherein the anti-human TSLP receptor antibody or the antigen-binding fragment thereof comprises a light chain constant region which is a human Igκ constant region.

7. The method for treating asthma according to claim 2, wherein the anti-human TSLP receptor antibody or the antigen-binding fragment thereof comprises a heavy chain constant region which is a human Igγ1 constant region and a light chain constant region which is a human Igκ constant region.

8. The method for treating asthma according to claim 3, wherein the anti-human TSLP receptor antibody comprises a heavy chain consisting of the amino acid sequence shown by SEQ ID NO: 1 and a light chain consisting of the amino acid sequence shown by SEQ ID NO: 3.

9. The method for treating asthma according to claim 2, wherein the antigen-binding fragment is a single-chain variable region fragment, Fab, Fab', or F(ab')$_2$.

10. The method for treating asthma according to claim 2, wherein the anti-human TSLP receptor antibody is an antibody comprising a heavy chain consisting of the amino acid sequence shown by SEQ ID NO: 1, wherein glutamic acid of the amino acid number 1 of SEQ ID NO: 1 is modified to pyroglutamic acid and/or lysine of the amino acid number 448 of SEQ ID NO: 1 is deleted, and a light chain consisting of the amino acid sequence shown by SEQ ID NO: 3.

11. The method for treating asthma according to claim 10, wherein the anti-human TSLP receptor antibody comprises a heavy chain consisting of the amino acid sequence of amino acid numbers 1 to 447 of SEQ ID NO: 1, and a light chain consisting of the amino acid sequence shown by SEQ ID NO: 3.

12. The method for treating asthma according to claim 1, wherein the anti-human TSLP receptor antibody or the antigen-binding fragment thereof is produced by a method comprising culturing a host cell to express an anti-human TSLP receptor antibody or an antigen-binding fragment thereof, wherein the host cell is selected from the group consisting of the following (a) and (b):

(a) a host cell transformed with an expression vector comprising a polynucleotide comprising a base sequence encoding a heavy chain variable region consisting of the amino acid sequence of amino acid numbers 1 to 118 of SEQ ID NO: 1 and a polynucleotide comprising a base sequence encoding a light chain variable region consisting of the amino acid sequence of amino acid numbers 1 to 108 of SEQ ID NO: 3;

(b) a host cell transformed with an expression vector comprising a polynucleotide comprising a base sequence encoding a heavy chain variable region consisting of the amino acid sequence of amino acid numbers 1 to 118 of SEQ ID NO: 1 and an expression vector comprising a polynucleotide comprising a base sequence encoding a light chain variable region consisting of the amino acid sequence of amino acid numbers 1 to 108 of SEQ ID NO: 3.

13. The method for treating asthma according to claim 1, wherein the anti-human TSLP receptor antibody is produced by a method comprising culturing a host cell to express an anti-human TSLP receptor antibody, wherein the host cell is selected from the group consisting of the following (a) and (b):

(a) a host cell transformed with an expression vector comprising a polynucleotide comprising a base sequence encoding a heavy chain consisting of the amino acid sequence shown by SEQ ID NO: 1 and a polynucleotide comprising a base sequence encoding a light chain consisting of the amino acid sequence shown by SEQ ID NO: 3;

(b) a host cell transformed with an expression vector comprising a polynucleotide comprising a base sequence encoding a heavy chain consisting of the amino acid sequence shown by SEQ ID NO: 1 and an expression vector comprising a polynucleotide comprising a base sequence encoding a light chain consisting of the amino acid sequence shown by SEQ ID NO: 3.

* * * * *

UNITED STATES PATENT AND TRADEMARK OFFICE
CERTIFICATE OF CORRECTION

PATENT NO. : 9,908,941 B2
APPLICATION NO. : 15/090051
DATED : March 6, 2018
INVENTOR(S) : Hiromu Sato et al.

It is certified that error appears in the above-identified patent and that said Letters Patent is hereby corrected as shown below:

In the Specification

Column 4, Line 64, after "administering" please insert --to a subject--
Column 16, Line 8, after "administering" please insert --to a subject--
Column 39, Lines 42-43, after "administering" please insert --to a subject--

Signed and Sealed this
Eighteenth Day of July, 2023

Katherine Kelly Vidal
*Director of the United States Patent and Trademark Office*